(12) United States Patent
Diomede et al.

(10) Patent No.: US 11,357,770 B2
(45) Date of Patent: Jun. 14, 2022

(54) METHOD OF TREATING IMMUNOGLOBULIN LIGHT CHAIN AMYLOIDOSIS

(71) Applicant: ALTERITY THERAPEUTICS LIMITED, Melbourne (AU)

(72) Inventors: Luisa Diomede, Milan (IT); Mario Salmona, Milan (IT); Giampaolo Merlini, Milan (IT)

(73) Assignee: Alterity Therapeutics Limited, Melbourne (AU)

( * ) Notice: Subject to any disclaimer, the term of this patent is extended or adjusted under 35 U.S.C. 154(b) by 0 days.

(21) Appl. No.: 16/311,428

(22) PCT Filed: Jun. 30, 2017

(86) PCT No.: PCT/AU2017/050678
§ 371 (c)(1),
(2) Date: Dec. 19, 2018

(87) PCT Pub. No.: WO2018/000047
PCT Pub. Date: Jan. 4, 2018

(65) Prior Publication Data
US 2019/0343825 A1    Nov. 14, 2019

(30) Foreign Application Priority Data
Jul. 1, 2016   (AU) .............................. 2016902594

(51) Int. Cl.
*A61K 31/4709*    (2006.01)
*A61P 39/04*    (2006.01)

(52) U.S. Cl.
CPC .......... *A61K 31/4709* (2013.01); *A61P 39/04* (2018.01)

(58) Field of Classification Search
CPC combination set(s) only.
See application file for complete search history.

(56) References Cited

U.S. PATENT DOCUMENTS

| 2007/0179123 A1 | 8/2007 | Chiang et al. |
| 2012/0277265 A1 | 11/2012 | Deraeve et al. |
| 2015/0335635 A1 | 11/2015 | Barnham et al. |

FOREIGN PATENT DOCUMENTS

| CN | 105367553 A | 3/2016 |
| WO | 02/24652 A1 | 3/2002 |
| WO | 2004007461 A1 | 1/2004 |
| WO | 2007056580 A2 | 5/2007 |
| WO | 2007118276 A1 | 10/2007 |
| WO | 2016183578 A1 | 11/2016 |
| WO | 2017027064 A1 | 2/2017 |

OTHER PUBLICATIONS

Blancas-Mejia (Systemic Amyloidoses, Annu Rev Biochem. 2013; 82: 745-774)(hereinafter Mejia).*
Blancas-Mejia, et al., "Systemic Amyloidoses", Annual Review of Biochemistry (2013), vol. 82, pp. 745-774.
Calabrese, et al., "Formation of a Stable Oligomer of Beta-2-Microglobulin Requires only Transient Encounter with Cu(II)", Journal of Molecular Biology (2007), vol. 367, No. 1, pp. 1-7.
Chang, et al., "An Improved Screening Model to Identify Inhibitors Targeting Zinc-Enhanced Amyloid Aggregation", Analytical Chemistry (2009), vol. 81, No. 16, pp. 6944-6951.
Deraeve, et al., "Preparation and Study of New Poly-8-Hydroxyquinoline Chelators for an Anti-Alzheimer Strategy", Chemistry—A European Journal (2008), vol. 14, No. 2, pp. 682-696.
Liang, et al., "Novel Fluorinated 8-Hydroxyquinolilne Based Metal Ionophores for Exploring the Metal Hypothesis of Alzheimer's Disease", ACS Medicinal Chemistry Letters (2015), vol. 6, pp. 1025-1029.
Supplementary European Search Report dated Jan. 27, 2020, 3 pages.
Bartolini, Manuela, et al., "Strategies for the Inhibition of Protein Aggregation in Human Diseases", Chembiochem, vol. 11, No. 8, (2010), pp. 1018-1035.
Diomede, Luisa, et al., "Cardiac Light Chain Amyloidosis: The Role of Metal Ions in Oxidative Stress and Mtiochondrial Damage", Antioxidants & Redox Signaling, vol. 27, No. 9, (2017), pp. 567-582.
Kladna, Aleksandra, et al., "Evaluation of the antioxidant activity of tetracycline antibiotics in vitro", Luminescence: The Journal of Biological and Chemical Luminescence, vol. 27, No. 4, (2011), pp. 249-255.
"Stoilova Journal of Medicinal Chemistry, 2013, vol. 56, No. 15, pp. 5987 to 6006".
Diomede, L., et al., "A Caenorhabditis elegans-based assay recognizes Immunoglobulin light chains causing heart amyloidosis", Blood, vol. 123, No. 23, Jun. 5, 2014, 3543-3552.

* cited by examiner

Primary Examiner — Kathrien A Cruz

(57) ABSTRACT

The present invention relates to the use of substituted quinoline compounds for treating immunoglobulin light chain (LC) amyloidosis (AL), especially cardiotoxicity associated with immunoglobulin LC AL. In particular, the substituted quinoline compounds useful in the treatment of cardiac LC amyloidosis are 5,7-dihalo-8-hydroxyquinoline derivatives, especially 5,7-dichloro-8-hydroxyquinoline derivatives.

17 Claims, 15 Drawing Sheets

B

C

METHOD OF TREATING IMMUNOGLOBULIN LIGHT CHAIN AMYLOIDOSIS

CROSS REFERENCE TO RELATED APPLICATIONS

This is a National Phase entry of International Application No. PCT/AU2017/050678, filed Jun. 30, 2017, which claims priority to Australian Patent Application No. 2016902594, filed Jul. 1, 2016, the disclosures of which are incorporated by reference in their entireties.

FIELD OF THE INVENTION

The present invention relates to the use of substituted quinoline compounds for treating immunoglobulin light chain (LC) amyloidosis (AL), especially cardiotoxicity associated with immunoglobulin LC AL. In particular, the substituted quinoline compounds useful in the treatment of cardiac LC amyloidosis are 5,7-dihalo-8-hydroxyquinoline derivatives, especially 5,7-dichloro-8-hydroxyquinoline derivatives.

BACKGROUND OF THE INVENTION

Organ damage in immunoglobulin light chains (LC) amyloidosis (AL) is caused by the toxic effects of aberrant, misfolded monoclonal LC that organize in extracellular amyloid deposits in target organs (Merlini and Bellotti, 2003; Merlini and Palladini, 2008). While the target organ may be any organ, with the exception of the central nervous system, common target organs include the kidneys and heart. Approximately 75% of patients with immunoglobulin LC AL manifest heart involvement at presentation. In most cases, these patients experience rapid worsening of cardiac failure with a median survival of only 6 months if cytotoxic chemotherapy fails to stop plasma-cell LC-production. Patients with advanced cardiac involvement (Wechalekar et al, 2013) are frequently too fragile to tolerate chemotherapy: paradoxically, patients most in need of treatment are those that at present cannot be managed effectively. New less toxic and more target oriented therapeutic approaches are needed in order to rescue this substantial proportion of patients.

There is a need for further therapies for treating, preventing or alleviating the symptoms of immunoglobulin LC AL, especially the cardiotoxicity associated with immunoglobulin LC AL.

SUMMARY OF THE INVENTION

In a first aspect, the present invention relates to a method of treating or preventing immunoglobulin light chain amyloidosis comprising administering to a subject a compound of formula (I):

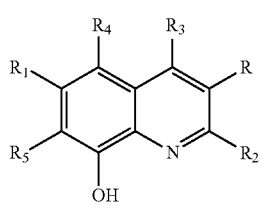

(I)

wherein R, $R^1$ and $R^3$ are the same or different and are each independently selected from hydrogen, $-C_{1-6}$ alkyl, $-C_{2-6}$ alkenyl, $-C_{2-6}$ alkynyl, $-C_{1-6}$ haloalkyl, $-OR^6$, $-SR^6$, $-NR^7R^8$, $-SOR^6$, $-SO_2R^6$, $-SO_2NR^7R^8$, $-C(O)R^9$, $-SO_3H$, halo, $-CN$, aryl and heterocyclyl;

$R^2$ is selected from $-(CH_2)_m$phenyl, $-(CH_2)_m$naphthyl, $-(CH_2)_m$tetrahydronaphthyl, $-(CH_2)_m$biphenyl, $-(CH_2)_m$ heterocyclyl, $-(CH_2)_mC(O)R^9$, $-(CH_2)_mC(S)R^9$, $-(CH_2)_mCN$, $-(CH_2)_mNR^7R^8$, $-CH=NR^6$, $-CH=NOR^6$, $-CH=N-NR^{10}R^{11}$, $-(CH_2)_mOR^6$, $-(CH_2)_mSR^6$ and $-(CH_2)_mSO_2NR^{10}R^{11}$;

$R^4$ and $R^5$ are the same or different and are independently selected from halo;

$R^6$ is selected from hydrogen, $-C_{1-6}$ alkyl, $-C_{2-6}$ alkenyl, $-C_{2-6}$ alkynyl, $-C_{1-6}$ haloalkyl, aryl and heteroaryl;

$R^7$ and $R^8$ are the same or different and are independently selected from hydrogen, $-C_{1-6}$ alkyl, $-C_{2-6}$ alkenyl, $-C_{2-6}$ alkynyl, $-C_{1-6}$ haloalkyl, $-(CH_2)_m$aryl and $-(CH_2)_m$heterocyclyl, or $R^7$ and $R^8$ taken together form a heterocyclic ring;

$R^9$ is selected from hydrogen, $-C_{1-6}$ alkyl, $-C_{2-6}$ alkenyl, $-C_{2-6}$ alkynyl, $-C_{1-6}$ haloalkyl, $-OR^6$, $-SR^6$, $-NR^7R^8$, aryl and heteroaryl;

$R^{10}$ and $R^{11}$ are the same or different and are independently selected from hydrogen, $-C_{1-6}$ alkyl, $-C_{2-6}$ alkenyl, $-C_{2-6}$ alkynyl, $-C_{1-6}$ haloalkyl, aryl and heteroaryl;

m is 0 or an integer selected from 1, 2 or 3;

wherein each alkyl, alkenyl, alkynyl, aryl and heteroaryl group may be optionally substituted;

or a pharmaceutically acceptable salt, hydrate or solvate thereof.

In some embodiments, the method is for the treatment or prevention of, or the alleviation or reversal of the symptoms of immunoglobulin LC AL, especially in which heart tissue is damaged. In particular embodiments, the method is for the treatment, prevention or the alleviation or reversal of the symptoms of cardiotoxicity associated with immunoglobulin LC AL.

In some embodiments, the method is for reversing the damage caused by cardiotoxic immunoglobulin LC comprising administering a compound of formula (I) or a pharmaceutically acceptable salt, hydrate or solvate thereof.

DETAILED DESCRIPTION OF THE INVENTION

Definitions

Figure 1:
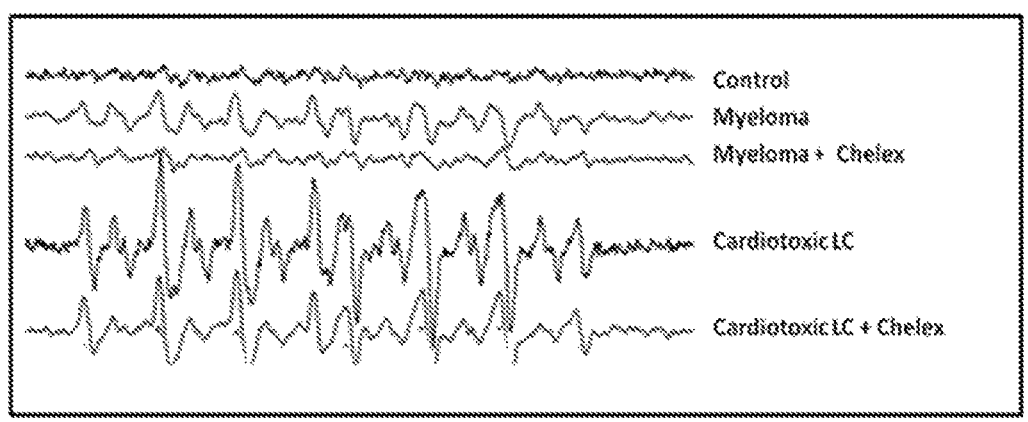
FIG. 1 provides Electron Paramagnetic Resonance spectra with spin-trap 5-(diethoxyphosphoryl)-5-methyl-1-pyrroline-N-oxide (DEPMPO) for MM2-BJ myeloma protein, MM2-BJ myeloma protein incubated with Chelex® resin, H7-BJ cardiotoxic LC, H7-BJ cardiotoxic LC incubated with Chelex® resin and a control (DEPMPO in 10 mM PBS). Experimental settings: microwave power 5 mW, microwave frequency 9.69 GHz, mod. Amplitude 1G, time constant 40.96 ms, sweep width 150G. EPR spectra of MM2-BJ (45 M) and H7BJ (28 M) dissolved in 10 mM PBS, pH 7.4, incubated with 1000-fold molar excess of DEPMPO. MM2-BJ 1 hr incubation with DEPMPO (70 scans). H7-BJ 5 hr incubation with DEPMPO (40 scans). Protein samples (100 g/mL) were incubated with 50 μM Chelex® resin for 10 minutes at 4° C., under shaking conditions. Samples were centrifuged at 8700×g for 5 minutes at 4° C. and supernatants collected. Protein concentration was determined using a Bio-Rad protein assay (Bio-Rad Laboratories GmbH, Munchen, Germany). Proteins were diluted in Chelex® treated PBS to give final concentrations of 45 μM for MM2-BJ (Myeloma+Chelex®) and 28 M for H7-BJ (Cardiotoxic LC+Chelex®) and DEPMPO was added in 1000-fold excess, incubation and EPR performed as above.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

Throughout this specification, unless the context requires otherwise, the words "comprise", "comprises" and "comprising" will be understood to imply the inclusion of a stated step or element or group of steps or elements but not the exclusion of any other step or element or group of steps or elements.

The term "alkyl" used either alone or in compound words such as "optionally substituted alkyl" or "haloalkyl" refers to straight chain, branched chain or cyclic hydrocarbon groups having from 1 to 10 carbon atoms, especially 1 to 6 carbon atoms or 1 to 4 carbon atoms. Illustrative of such alkyl groups are methyl, ethyl, propyl, 1-methylethyl, butyl, 2-methylpropyl, 1,1-dimethylethyl, 2,2-dimethylpropyl, 1-methylpropyl, 1,1-dimethylpropyl, 1,2-dimethylpropyl, 1,1-dimethylbutyl, 1,2-dimethylbutyl, 1,3-dimethylbutyl, 2,2-dimethylbutyl, 3,3-dimethylbutyl, pentyl, hexyl, heptyl, octyl, nonyl, decyl, cyclopropyl, cyclobutyl, cyclopentyl, cyclohexyl, cycloheptyl and cyclooctyl.

The term "alkenyl" used either alone or in compound words such as "optionally substituted alkenyl", denotes linear, branched or mono- or poly-cyclic radicals having at least one carbon-carbon double bond and 2 to 20 carbon atoms, especially 2 to 14 carbon atoms or 2 to 6 carbon atoms. Examples of alkenyl radicals include allyl, ethenyl, propenyl, butenyl, 2-methylpropenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl, 1,3,5,7-cycloocta-tetraenyl and the like.

The term "alkynyl" used either alone or in compound words such as "optionally substituted alkynyl", denotes linear or branched radicals having at least one carbon-carbon triple bond and 2 to 10 carbon atoms, especially 2 to 6 carbon atoms or 2 to 4 carbon atoms. Examples of alkynyl radicals include ethynyl, propynyl, butynyl, 1-pentynyl, 4-penynyl, 1-hexynyl, 3-hexynyl, 5-hexynyl, 1-heptynyl, 3-heptynyl, 6-heptynyl, 1-octynyl, 7-octynyl, 1-nonynyl, 2-nonynyl, 3-nonynyl, 8-nonynyl, 1-decynyl, 3-decynyl, 9-decynyl and the like.

The terms "halo" or "halogen" refer to fluorine, chlorine, bromine or iodine.

The term "haloalkyl" refers to an alkyl group as described above in which one or more hydrogen atoms are replaced by a halogen, especially a fluorine atom. Illustrative examples of haloalkyl groups include trifluoromethyl, difluoromethyl, fluoromethyl, 2-fluoroethyl, 2,2-difluoroethyl, 2,2,2-trifluoroethyl, 1-fluoroethyl, 1,1-difluoroethyl, 1,1,2,2,2-pentafluoroethyl, 3-fluoropropyl, 4-fluorobutyl, 5-fluoropentyl, 6-fluorohexyl, trichloromethyl, dichloromethyl, chloromethyl, 2-chloroethyl, 2,2-dichloroethyl, 2,2,2-trichloroethyl, 1-chloroethyl, 1,1-dichloroethyl, 1,1,2,2,2-pentachloroethyl, 3-chloropropyl, 4-chlorobutyl, 5-chloropentyl, 6-chlorohexyl, chlorodifluoromethyl, chlorofluoromethyl, bromomethyl, 2-bromoethyl, 2-bromo-2-chloroethyl, 2-chloro-2-fluoroethyl, 2-chloro-2,2-difluoroethyl and the like.

The term "aryl" used either alone or in compound words such as "optionally substituted aryl" denotes a carbocyclic aromatic system containing one, two or three rings wherein such rings may be attached together in a pendent manner or may be fused. The term "aryl" embraces aromatic radicals such as phenyl, naphthyl, tetrahydronaphthyl, indane fluorene, phenanthrene and biphenyl. In particular embodiments, the aryl is a 5- or 6-membered aryl such as phenyl.

The term "heterocyclic" or "heterocyclyl" as used herein, refers to a cyclic hydrocarbon which is monocyclic, bicyclic or tricyclic and in which one or more carbon atoms have been replaced by heteroatoms independently selected from the group consisting of N, N(R), S, S(O), S(O)$_2$ and O. A heterocyclic ring may be saturated or unsaturated or aromatic. Examples of suitable heterocyclyl groups include azetidine, tetrahydrofuranyl, tetrahydrothiophenyl, pyrrolidinyl, 2-oxopyrrolidinyl, pyrrolinyl, pyranyl, dioxolanyl, piperidinyl, 2-oxopiperidinyl, pyrazolinyl, imidazolinyl, thiazolinyl, dithiolyl, oxathiolyl, dioxanyl, dioxinyl, dioxazolyl, oxathiozolyl, oxazolonyl, piperazinyl, morpholino, thiomorpholinyl, 3-oxomorpholinyl, dithianyl, trithianyl, oxazinyl, acridinyl, carbazolyl, cinnolinyl, quinoxalinyl, quinazolinyl, pyrazolyl, indolyl, isoindolyl, 1H,3H-1-oxoisoindolyl, benzotriazolyl, furanyl, thienyl, thiophenyl, benzothienyl, benzofuranyl, benzodioxane, benzodioxin, quinolinyl, isoquinolinyl, oxazolyl, isoxazolyl, imidazolyl, pyrazinyl, pyridazinyl, pyridinyl, pyrimidinyl, pyrrolyl, tetrahydroquinolinyl, thiazolyl, isothiazolyl, 1,2,3-triazolyl, 1,2,4-triazolyl, 1,2,4-oxadiazolyl, 1,2,4-thiadiazolyl, 1,3,5-triazinyl, 1,2,4-triazinyl, 1,2,4,5-tetrazinyl, tetrazolyl, carbazolyl, xanthenyl, acridinyl, phenazinyl, phenothiazinyl, phenoxazinyl, azepinyl, oxepinyl and thiepinyl. Particular heterocyclyl groups have 5- or 6-membered rings, such as tetrahydrofuranyl, tetrahydrothiophenyl, pyrrolidinyl, pyrrolinyl, piperidinyl, pyrazolyl, pyrazolinyl, imidazolinyl, piperazinyl, morpholino, thiomorpholinyl, furanyl, thienyl, oxazolyl, indolyl, isoindolyl, 1H,3H-1-oxoisoindolyl, isoxazolyl, imidazolyl, pyrazinyl, pyridazinyl, pyridinyl, pyrimidinyl, pyrrolyl, thiazolyl, isothiazolyl, 1,2,3-triazolyl, 1,2,4-triazolyl and 1,2,4-oxadiazolyl and 1,2,4-thiadiazolyl.

The term "optionally substituted" refers to a group which may or may not be further substituted with one or more groups selected from alkyl, alkenyl, alkynyl, aryl, aldehyde, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy, mercapto, alkylthio, benzylthio, acylthio, cyano, phosphorus-containing groups and the like. In particular embodiments, the optional substituent is $C_{1-6}$ alkyl, especially $C_{1-4}$ alkyl; $C_{1-6}$ haloalkyl, especially $C_{1-4}$ haloalkyl; fluorine; chlorine; iodine; cyano; $C_{1-6}$ alkoxy, especially $C_{1-4}$ alkoxy; aryl; heterocyclyl; amino; alkylamino or dialkylamino.

The salts of the compound of Formula I are preferably pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulphuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

In addition, some of the compounds of the present invention may form solvates with water (hydrates) or common organic solvents. Such solvates are encompassed within the scope of the invention. In some embodiments, the solvate is a hydrate or hemihydrate. In some embodiments, the solvate is a monohydrate. In other embodiments, the solvate is a methanol solvate.

As used herein, the term "amyloidosis" or AL refers to diseases which result from the extracellular deposition of fibril-forming monoclonal immunoglobulin (Ig) light chains, most commonly of the lambda isotype. The abnormal Ig light chains have an unstable conformation and undergo abnormal folding allowing them to stack together to form amyloid fibrils. The abnormal light chains are usually secreted by plasma cells. The abnormal light chains may be deposited in any organ, with the exception of the central nervous system, causing organ damage. The abnormal light chains are cardiotoxic when deposited in the heart and result in heart damage.

Methods of the Invention

The methods of the present invention relate to the treatment or prevention of immunoglobulin light chain amyloidosis in a subject, especially a human.

The amyloidosis may occur in any organ including heart, kidney, autonomic or peripheral nervous systems, gastrointestinal tract, lung and liver. In particular embodiments, the amyloidosis occurs in the heart.

In some embodiments, the methods relate to the treatment or prevention of cardiotoxicity associated with immunoglobulin light chain amyloidosis.

In some embodiments, the methods relate to the alleviation of the symptoms associated with immunoglobulin light chain amyloidosis or cardiotoxicity associated with immunoglobulin light chain amyloidosis.

In other embodiments, the methods relate to reversing the damage caused by cardiotoxic immunoglobulin LC, especially in heart tissue.

In some embodiments, the immunoglobulin LC is of the lambda isotype.

Symptoms associated with cardiotoxic immunoglobulin LC AL include thickening of the ventricular and atrial walls, restrictive cardiopathy, asthenia, dyspnoea and limb oedema. Infiltration of the cardiac muscle by immunoglobulin LC may also induce conduction disorders and ventricular or supraventricular arrhythmias. These symptoms, may be reversed, alleviated, treated or prevented by the methods of the invention.

The compounds used in the methods of the invention are 5,7-dihalo-8-hydroxyquinoline compounds of formula (I):

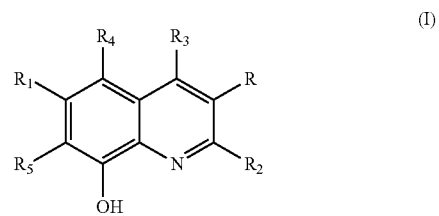

wherein R, $R^1$ and $R^3$ are the same or different and are each independently selected from hydrogen, —$C_{1-6}$ alkyl, —$C_{2-6}$ alkenyl, —$C_{2-6}$ alkynyl, —$C_{1-6}$ haloalkyl, —$OR^6$, —$SR^6$, —$NR^7R^8$, —$SOR^6$, —$SO_2R^6$, —$SO_2NR^7R^8$, —$C(O)R^9$, —$SO_3H$, halo, —CN, aryl and heterocyclyl;

$R^2$ is selected from —$(CH_2)_m$phenyl, —$(CH_2)_m$naphthyl, —$(CH_2)_m$tetrahydronaphthyl, —$(CH_2)_m$biphenyl, —$(CH_2)_m$ heterocyclyl, —$(CH_2)_mC(O)R^9$, —$(CH_2)_mC(S)R^9$, —$(CH_2)_mCN$, —$(CH_2)_mNR^7R^8$, —CH=$NR^6$, —CH=$NOR^6$, —CH=N—$NR^{10}R^{11}$, —$(CH_2)_mOR^6$, —$(CH_2)_mSR^6$ and —$(CH_2)_mSO_2NR^{10}R^{11}$;

$R^4$ and $R^5$ are the same or different and are independently selected from halo;

$R^6$ is selected from hydrogen, —$C_{1-6}$ alkyl, —$C_{2-6}$ alkenyl, —$C_{2-6}$ alkynyl, —$C_{1-6}$ haloalkyl, aryl and heteroaryl;

$R^7$ and $R^8$ are the same or different and are independently selected from hydrogen, —$C_{1-6}$ alkyl, —$C_{2-6}$ alkenyl, —$C_{2-6}$ alkynyl, —$C_{1-6}$ haloalkyl, —$(CH_2)_m$aryl and —$(CH_2)_m$heterocyclyl, or $R^7$ and $R^8$ taken together form a heterocyclic ring;

$R^9$ is selected from hydrogen, —$C_{1-6}$ alkyl, —$C_{2-6}$ alkenyl, —$C_{2-6}$ alkynyl, —$C_{1-6}$ haloalkyl, —$OR^6$, —$SR^6$, —$NR^7R^8$, aryl and heteroaryl;

$R^{10}$ and $R^{11}$ are the same or different and are independently selected from hydrogen, —$C_{1-6}$ alkyl, —$C_{2-6}$ alkenyl, —$C_{2-6}$ alkynyl, —$C_{1-6}$ haloalkyl, aryl and heteroaryl;

m is 0 or an integer selected from 1, 2 or 3;

wherein each alkyl, alkenyl, alkynyl, aryl and heteroaryl group may be optionally substituted;

or a pharmaceutically acceptable salt, hydrate or solvate thereof.

In particular embodiments, one or more of the following applies:

Each R, $R^1$ and $R^3$ are independently selected from hydrogen, —$C_{1-3}$ alkyl, —$C_{2-3}$ alkenyl, —$C_{2-3}$ alkynyl, —$CF_3$, —$CHF_2$, —$CH_2F$, —$CH_2CF_3$, —$CH_2CF_2H$, —$CH_2CH_2F$, —OH, —$OC_{1-6}$ alkyl, —$OCF_3$, —$OCHF_2$, —$OCH_2F$, —$OCH_2CF_3$, —$OCH_2CHF_2$, —$OCH_2CH_2F$, —$OC_{2-3}$ alkenyl, —$OC_{2-3}$ alkynyl, —$NH_2$, —NH($C_{1-3}$ alkyl), —N($C_{1-3}$ alkyl)$_2$, —$SO_2C_{1-6}$ alkyl, —$CO_2H$, —$CO_2C_{1-3}$ alkyl, —$CONH_2$, —$CONH(C_{1-3}$ alkyl), —$CON(C_{1-3}$ alkyl)$_2$, F, Cl and Br; especially hydrogen, —$C_{1-3}$ alkyl, —$CF_3$, —$OC_{1-3}$ alkyl, —$OCF_3$, —$NH_2$, —$CO_2H$, —$CONH_2$, F and Cl, more especially hydrogen, methyl, ethyl, —$CF_3$, methoxy, ethoxy, —$OCF_3$ and F, most especially hydrogen;

$R^2$ is selected from —$(CH_2)_m$heterocyclyl, —$(CH_2)_mC(O)R^9$, —$(CH_2)_mCN$, —$(CH_2)_mNR^7R^8$, —CH=$NC_{1-6}$ alkyl, —CH=N—$OR^6$, —CH=N—$NR^{10}R^{11}$, —$SO_2NR^{10}R^{11}$ and —$(CH_2)_mOR^6$; especially heterocyclyl, —$CH_2$heterocyclyl, —$CO_2H$, —$C(O)NR^7R^8$, —$NR^7R^8$, —$CH_2NR^7R^8$, —CH=NOH, —CH=$NOC_{1-6}$ alkyl, —$CH_2OR^6$ or —$SO_2NR^{10}R^{11}$, more especially pyrrolyl, pyrrolinyl, imidazolyl, pyrazolyl, pyridyl, pyrimidinyl, pyrazinyl, pyridazinyl, triazolyl, particularly when the attachment of the heterocyclyl group to the quinolinyl group is at a carbon atom of the heterocyclyl group adjacent to a nitrogen atom of the heterocyclyl group, —C(O)NH(C$_{1-6}$ alkyl), —C(O)NH(CH$_2$heterocyclyl), —C(O)NH (CH$_2$CH$_2$heterocyclyl), —C(O)NH (CH$_2$CH$_2$CH$_2$heterocyclyl, —CH$_2$NH$_2$, —CH$_2$NH(C$_{1-3}$ alkyl), —CH$_2$N(C$_{1-3}$ alkyl)$_2$, —CH$_2$NH(heterocyclyl), —CH$_2$N(C$_{1-3}$ alkyl)(heterocyclyl), —CH$_2$N(C$_{1-3}$ alkyl) (CH$_2$heterocyclyl), —CH$_2$N(C$_{1-3}$ alkyl)(C$_{2-3}$ alkenyl), —CH$_2$N(C$_{1-3}$ alkyl)(C$_{2-3}$ alkynyl), —N(C$_{1-3}$ alkyl)$_2$, —N(C$_{1-3}$ alkyl)(heterocyclyl), —CH=NC$_{1-3}$ alkyl, —CH=NOH, —CH=NO(C$_{1-3}$ alkyl), —CH$_2$OC$_{1-6}$ alkyl, —CH$_2$OC$_{1-6}$ haloalkyl, most especially —C(O)NH (CH$_2$heterocyclyl), —C(O)NH(CH$_2$CH$_2$heterocyclyl), pyridyl, —CH$_2$N(C$_{1-3}$ alkyl)$_2$, —N(C$_{1-3}$ alkyl)(heterocyclyl), —CH$_2$NH(C$_{1-3}$ alkyl), —CH=N—OH, —CH=N—OCH$_3$, —CH$_2$OC$_{1-6}$ alkyl, —CH$_2$OC$_{1-6}$ haloalkyl, —CH=NCH$_3$ and —CH$_2$N(C$_{1-3}$ alkyl)(CH$_2$heterocyclyl);

m is 0 or an integer of 1 or 2, especially 0 or 1;

$R^4$ and $R^5$ are independently selected from F, Cl, Br or I, especially F or Cl or I, more especially $R^4$ and $R^5$ are both Cl.

In particular embodiments, the compound of formula (I) is selected from:

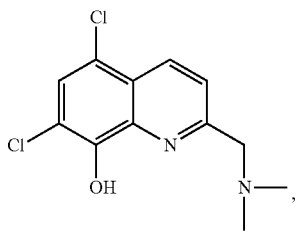

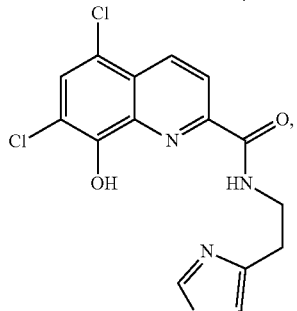

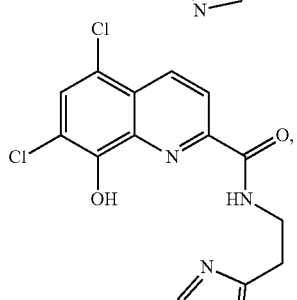

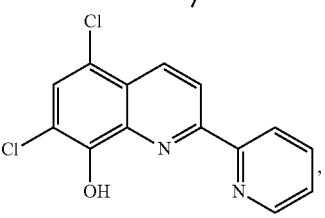

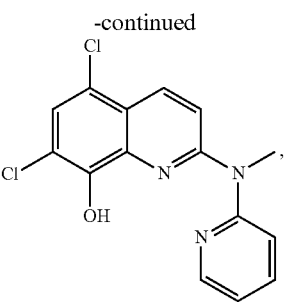

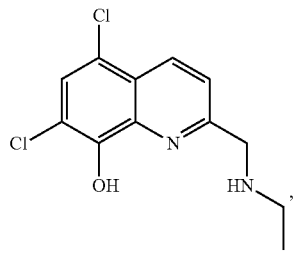

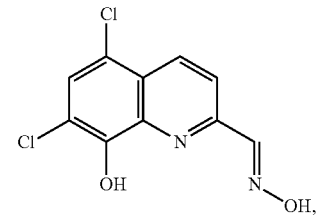

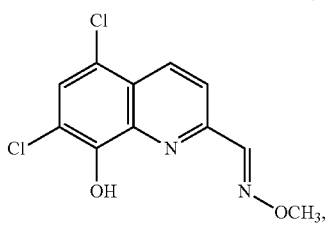

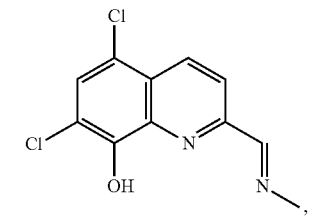

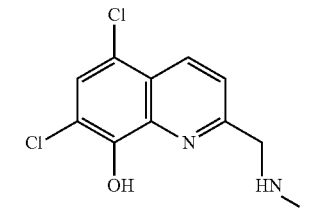

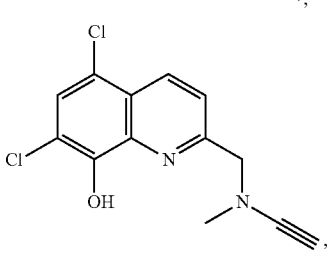

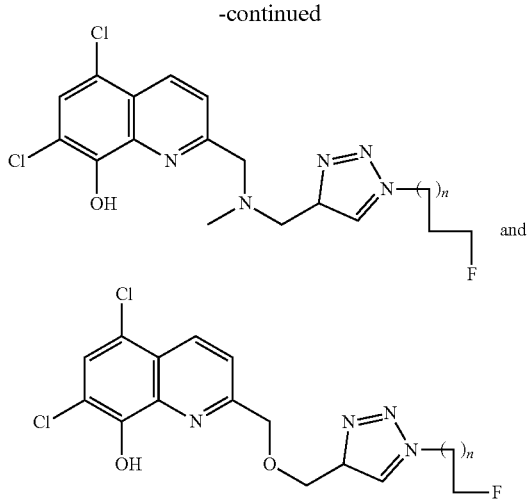

where n is 1, 2 or 3;
especially

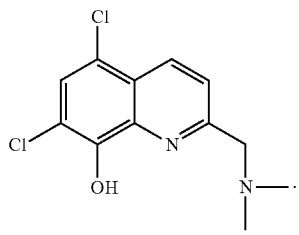 [SMILES: CN(C)Cc1ccc2c(Cl)cc(Cl)c(O)c2n1]
(1033)

The compounds of formula (I) may be prepared by methods known in the art. For example suitable methods of synthesis are provided in WO2004/007461 and Liang et al, 2015.

The term "subject" as used herein refers to any animal having a disease or condition which requires treatment for immunoglobulin light chain amyloidosis. The subject may be a mammal, preferably a human, or may be a domestic or companion animal. While it is particularly contemplated that the compounds of the invention are suitable for use in medical treatment of humans, it is also applicable to veterinary treatment, including treatment of companion animals such as dogs and cats, and domestic animals such as horses, ponies, donkeys, mules, llama, alpaca, pigs, cattle and sheep, or zoo animals such as primates, felids, canids, bovids, and ungulates.

Suitable mammals include members of the Orders Primates, Rodentia, Lagomorpha, Cetacea, Carnivora, Perissodactyla and Artiodactyla. Members of the Orders Perissodactyla and Artiodactyla are particularly preferred because of their similar biology and economic importance.

For example, Artiodactyla comprises approximately 150 living species distributed through nine families: pigs (Suidae), peccaries (Tayassuidae), hippopotamuses (Hippopotamidae), camels (Camelidae), chevrotains (Tragulidae), giraffes and okapi (Giraffidae), deer (Cervidae), pronghorn (Antilocapridae), and cattle, sheep, goats and antelope (Bovidae). Many of these animals are used as feed animals in various countries. More importantly, many of the economically important animals such as goats, sheep, cattle and pigs have very similar biology and share high degrees of genomic homology.

The Order Perissodactyla comprises horses and donkeys, which are both economically important and closely related. Indeed, it is well known that horses and donkeys interbreed.

As used herein, the term "therapeutically effective amount" is meant an amount of a compound of the present invention effective to yield a desired therapeutic response, for example, to prevent or treat amyloidosis or alleviate or reverse the symptoms of amyloidosis.

The specific "therapeutically effective amount" will, obviously, vary with such factors as the particular condition being treated, the physical condition of the subject, the type of subject being treated, the duration of the treatment, the nature of concurrent therapy (if any), and the specific formulations employed and the structure of the compound or its derivatives.

It is expected that the amount will fall in a relatively broad range that can be determined through routine trials. An effective amount in relation to a human patient, for example, may lie in the range of about 0.1 ng per kg of body weight to 1 g per kg of body weight per dosage. The dosage is preferably in the range of 1 ng to 1 g per kg of body weight per dosage, such as is in the range of 1 ng to 1 mg or 1 mg to Ig per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another embodiment, the dosage is in the range of 1 mg to 100 mg per kg of body weight per dosage, such as up to 50 mg per kg of body weight per dosage. In yet another embodiment, the dosage is in the range of 1 µg to 1 mg per kg of body weight per dosage. In another embodiment, the dosage is in the range of 1 ng to 1 mg, for example, 1 ng to 500 ng, 1 ng to 250 ng or 1 ng to 100 ng. In embodiments where the compound is administered with another medicament to provide a synergistic effect, lower amounts of compound may be required for administration. Dosage regimes may be adjusted to provide the optimum therapeutic response. For example, several divided doses may be administered daily, weekly, monthly or other suitable time intervals, or the dose may be proportionally reduced as indicated by the exigencies of the situation The compounds of the present invention may additionally be combined with other medicaments to provide an operative combination. It is intended to include any chemically compatible combination of pharmaceutically-active agents, as long as the combination does not eliminate the activity of the compound of formula I. It will be appreciated that the compound of the invention and the other medicament may be administered in a single composition or may be administered separately, sequentially or simultaneously.

The compounds used in the methods may be combined with antioxidants such as tetracycline (TETRA), N-acetyl cysteine (NAC), α-tocopherol, carvedilol, pirfenidone, ascorbic acid, glutathione, melatonin and polyphenols such as resveratrol, ellagic acid, gallic acid and tannic acid.

Alternatively, the compounds used in the methods of the invention may be combined with other pharmaceutical compounds that are useful in treating amyloidosis including pomalidomide, lenalidomide, thalidomide, bendamustine, bortezomib, melphalan, dexamethasone, interferon alpha, human immune globulin, iododoxorubicin, revlimid, cyclophosphamide, filgrastin, sargramostim, busulfan, amifostine, MLN9708, Enbrel, carfilzomib, doxycycline, imatinib mesylate, velcade, diuretics such as furosemide, torsemide, ethacrynic acid, thiazides, carbonic anhydrase inhibitors, aldosterone antagonists, amiloride and triamterene; and antiarrythmic drugs such as quinidine, procainamide, disopyramide, lidocaine, phenytoin, mexiletine, tocainide, encainide, flecainide, propafenone, moricizine, carvedilol, propranolol, esmolol, timolol, metoprolol, atenolol, bisoprolol, amiodarone, sotalol, ibutilide, dofetilide, dronedarone, E-4031, verapamil, diltiazem, adenosine, digoxin and magnesium sulphate or combinations thereof.

In some embodiments, the combination of compound of formula (I) and other pharmaceutical agent may demonstrate a synergistic effect.

In another aspect of the present invention there is provided a method of treating or preventing immunoglobulin LC AL comprising administering to a subject in need thereof, a compound of formula (I) as defined above or a pharmaceutically acceptable salt, hydrate or solvate thereof and an antioxidant.

In particular embodiments, the compound of formula (I) is

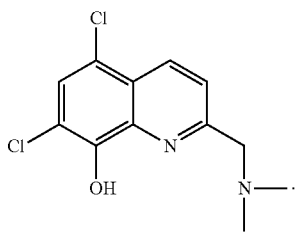

In some embodiments, the antioxidant is tetracycline.

In another aspect of the invention there is provided a use of a compound of formula (I) as defined above, in the manufacture of a medicament for treating immunoglobulin light chain amyloidosis in a subject.

Also provided is a compound of formula (I) as defined above for use in treating immunoglobulin light chain amyloidosis in a subject.

In yet another aspect of the invention there is provided a use of a compound of formula (I) as defined above in the manufacture of a medicament for treating or preventing or alleviating or reversing the symptoms of cardiotoxicity associated with immunoglobulin light chain amyloidosis in a subject.

In a further aspect of the invention there is provided a compound of formula (I) as defined above for use in treating or preventing or alleviating or reversing the symptoms of cardiotoxicity associated with immunoglobulin light chain amyloidosis in a subject.

In a further aspect of the invention there is provided a use of a compound of formula (I) as defined above in the manufacture of a medicament for treating or preventing or alleviating or reversing the symptoms of immunoglobulin light chain amyloidosis.

In yet another aspect of the invention there is provided a compound of formula (I) as defined above for use in treating or preventing or alleviating or reversing the symptoms of immunoglobulin light chain amyloidosis.

Compositions

While it is possible that, for use in therapy, a compound of the invention may be administered as a neat chemical, it is preferable to present the active ingredient as a pharmaceutical composition comprising the active ingredient and one or more pharmaceutically acceptable carriers.

The carrier(s) must be "acceptable" in the sense of being compatible with the other ingredients of the composition and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation. The compounds of the invention, together with a conventional adjuvant, carrier, excipient, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

Formulations containing ten (10) milligrams of active ingredient or, more broadly, 0.01 to two hundred (200) milligrams, per tablet, are accordingly suitable representative unit dosage forms. The compounds of the present invention can be administered in a wide variety of oral and parenteral dosage forms. It will be obvious to those skilled in the art that the following dosage forms may comprise, as the active component, either a compound of the invention or a pharmaceutically acceptable salt, hydrate or solvate of the compound of formula (I).

For preparing pharmaceutical compositions from the compounds of formula (I), pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired. The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds of formula (I) may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomizing spray pump. To improve nasal delivery and retention the compounds according to the invention may be encapsulated with cyclodextrins, or formulated with their agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example, dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP).

Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 1 to 10 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compositions may comprise further active ingredients such as therapies for treating immunoglobulin LC amyloidosis, especially cardiotoxicity associated with immunoglobulin LC amyloid deposits.

The invention will now be described with reference to the following Examples which illustrate some preferred aspects of the present invention. However, it is to be understood that the particularity of the following description of the invention is not to supersede the generality of the preceding description of the invention.

EXAMPLES

Example 1: Preparation of Protein Samples

Human Samples.

Urine, bone marrow plasma cells and endomyocardial biopsies were obtained from patients during routine diagnostic procedures at the Amyloid Research and Treatment Centre, Foundation IRCCS Policlinico San Matteo (Pavia, Italy). Acquisition, storage and use of biological samples for research purposes were approved by the Institutional Review Board. Written informed consent was received from participants prior to inclusion in the study. The presence of tissue amyloid deposits and amyloid organ involvement were defined according to the International Consensus Panel Criteria (Gertz et al. 2004). In particular, LC cardiotoxicity was evaluated on the basis of clinical, instrumental (echocardiography) and biochemical parameters. Non amyloidogenic LC from multiple myeloma patients (MM) were used as controls. All LC included in the study were λ isotype, which represent ~75% of amyloidogenic LCs. The clinical characteristics of the patients included in the study are reported in Table 1A. Endomyocardial biopsies from 3 AL patients with advanced cardiac dysfunction (Table 1B) and from 1 subject with primary dilated cardiomyopathy, used as controls for disease and severity of heart dysfunction, were analyzed.

Abbreviations for Tables 1A and B

M, male; F, female; ° According to Gertz 2005; H, Heart; °° According to the International Consensus Panel criteria; BJ, Bence Jones; n.a., not available; pI, isoelectric point; FLC, Free Light Chains; BNP, Brain Natriuretic Peptide; cTnI, cardiac Troponin I; IVS, Interventricular Septum; PW, Posterior Wall; EF, Ejection Fraction. § Entirely constituted by BJ proteins. Reference ranges: serum λ FLC <26.3 mg/L, κ/λ ratio 0.26-1.65; serum creatinine <1.18 mg/dL in men, <1.02 mg/dL in women; NT-proBNP <332 ng/L; BNP, <50 ng/L; cTnI <0.04 ng/mL. * BNP (ng/L).

mined using the Pierce BCA Protein Assay Kit (Thermo Scientific, Rockford, Ill., USA) and bovine serum albumin as standard. Recombinant full-length H7-r LC was produced in *E. coli* (Rognoni et al., 2013; Perfetti et al., 1996). Nucleotide sequences of LC from H7 patient were obtained using a universal inverse-PCR strategy (Perfetti et al., 1996). In order to determine germline gene, nucleotide sequence alignments were made using the current releases of EMBL-GenBank, V-BASE (V-BASE Sequence Directory, MRC Centre for Protein Engineering, Cambridge, UK) and IMGT sequence directories.

Example 2: Generation of Oxygen Radicals

To investigate the involvement of metal ions in radical generation, MM2-BJ and H7-BJ (100 μg/mL) in 10 mM PBS, pH 7.4, were incubated with or without 50 μM Chelex® 100 metal chelating resin (Biorad) for 10 min at 4°

TABLE 1

Clinical and biochemicals characteristics of (A) patients at diagnosis of immunoglobulin light chain amyloidosis (AL) or multiple myeloma (MM)

A

| Code | Gender, age | Cardiac stage° | Diagnosis | Organs Involved°° | Biochemical source and characteristics | | | | Serum λ | | Protein-uria | Crea-tinine | Cardiac parameters | | | | |
|---|---|---|---|---|---|---|---|---|---|---|---|---|---|---|---|---|---|
| | | | | | Recombinant | BJ | Germline gene | Deduced MW (kDa)/pI | FLC (mg/L) | κ/λ FLC ratio | (g/24 h) | (mg/dl) | NT-proBNP (ng/L) | cTnI (ng/mL) | IVS (mm) | PW (mm) | EF (%) |
| H6 | M, 74 | III | AL | H | | x | IGLV6-57 | 23.2/5.37 | 683 | 0.009 | 0.45 | 0.73 | 4300 | 0.2 | 15 | 15 | 42 |
| H7 | M, 45 | III | AL | H | x | x | IGLV1-51 | 22.3/6.15 | 477 | 0.01 | 0.33 | 0.98 | 8882 | 0.16 | 19 | 19 | 45 |
| H18 | M, 69 | III | AL | H | | x | IGLV3-19 | 22.7/5.88 | 509 | 0.01 | 0.82 | 0.97 | 3839 | 0.34 | 21 | 18 | 61 |
| MM2 | F, 71 | | MM | — | | x | IGLV3-19 | 22.8/5.61 | 6130 | 0.001 | 0.52§ | 2.07 | 42* | 0.007 | 9 | 9 | 65 |
| MM4 | M, 65 | | MM | — | | x | IGLV2-23 | 22.7/7.72 | 1140 | 0.001 | 0.12§ | 0.89 | 201 | n.a. | 10 | 10 | 64 |
| MM7 | M, 48 | | MM | — | | x | n.a. | n.a. | 573 | 0.01 | 1.87§ | 0.84 | 14.5 | 0.003 | 10 | 10.5 | 67 |

B

| Code | Gender, age | Cardiac stage° | Germline gene | Serum λ FLC (mg/L) | NT-proBNP (ng/L) | cTnI (ng/mL) | IVS (mm) | PW (mm) | EF (%) |
|---|---|---|---|---|---|---|---|---|---|
| AL1 | F, 52 | III | IGLV3-1 | 776 | 4325 | 0.049 | 11 | n.a. | 55 |
| AL2 | M, 73 | III | IGLV1-44 | 59 | 7182 | 0.09 | 15 | 14 | 51 |
| AL3 | M, 71 | III | n.a. | 218 | 10914 | 0.1 | 16 | 16 | 50 |

Lc Purification.

Human monoclonal LC were isolated from 24 h urine (Bence Jones, BJ) and by production, as recombinant proteins (r), in a bacterial system (Rognoni et al. 2013), from patients affected by AL amyloidosis or MM. Overall, 7 proteins were obtained (6 BJ and 1 recombinant LC) (Table 1A).

LC were purified by anion exchange chromatography on an AKTÄ Purifier® FPLC system (GE-Healthcare, Piscataway, N.J., USA), using a HiPrep16/10 Q FF column, equilibrated in 20 mM sodium phosphate, pH 7.0. Bound proteins were eluted with a 0 up to 1 M NaCl linear gradient. MM4-BJ was purified using a cation exchanger column (HiPrep16/10 SP FF), equilibrated in 20 mM Tris-HCl, pH 8.0, and was eluted with a 0 up to 1 M NaCl linear gradient. The homogeneity of the isolated species was assessed by 12% SDS-PAGE. The final protein concentration was deter- C., under shaking conditions. PBS and bidistilled water were also incubated with Chelex®, in the same conditions. Samples were centrifuged at 8700 g×5 min at 4° C. and the supernatants were collected. The protein content was then determined using a Bio-Rad Protein assay (Bio-Rad Laboratories GmbH, Munchen, Germany). Proteins were then diluted in Chelex®-treated 10 mM PBS, pH 7.4, at a final concentration of 45 μM for MM2-BJ and 28 μM for H7-BJ. Detection of oxygen radical species (specifically superoxide) by EPR spectroscopy was evaluated by adding the spin-trap 5-diethoxyphosphoryl-5-methyl-1-pyrroline-N-oxide (DEPMPO, Enzo Life Sciences), with a 1000-fold molar excess, as already described (Diomede et al., 2014). Samples were incubated at 37° C. in the dark and EPR spectra were recorded at room temperature using a quartz flat cell, on an ESP300 CW-X band spectrometer (Bruker) equipped with a cylindrical cavity. EPR spectra simulations were done with the WinSim software (version 0.96) developed by D. Duling (Public EPR Software Tools, NIH, USA).

Cardiotoxic H7-BJ generated significantly higher levels of superoxide than MM2-BJ control protein as shown in FIG. 1. Free radical generation by MM2-BJ control was abolished by elution on Chelex® resin. The generation of free radicals by H7-BJ was significantly attenuated when the protein was eluted on Chelex® resin.

Example 3: Generation of $H_2O_2$ $H_2O_2$ is a product of metabolic activity which of itself is not a free radical, but because it can readily react to generate free radicals (eg in the presence of a redox active metal), it is described as a "reactive oxygen species" (ROS).

Amplex Red $H_2O_2$ assay.

H7-BJ and MM2-BJ proteins (100 μg/mL) in 10 mM sodium phosphate buffer (PB), pH 7.4, were incubated at room temperature in the presence or absence of 50 μM Chelex® resin or 2 nM 5,7-dichloro-8-hydroxy-2-(dimethylaminomethyl)quinoline (1033). Different times after incubation (0-2 h), 2 μL of solutions were put into a 96-well black plate, diluted 1:100 (vol/vol) with 10 mM PBS, pH 7.4, and the amount of $H_2O_2$ generated was determined by using the Amplex Red assay kit (Molecular probes, Life Technologies). To this end, 50 μL working solution of 100 μM Amplex Red and 200 mU/mL horseradish peroxidase in 10 mM PB, pH 7.4, was added to each well. The plate was shaken and incubated at room temperature for 30 min, protected from light. The fluorescence was read on a Tecan Infinite M200 microplate reader (Tecan, Austria) at excitation wavelength of 563 nm and emission wavelength of 587 nm. Averages and standard deviations were converted to $H_2O_2$ concentrations.

Figure 2:
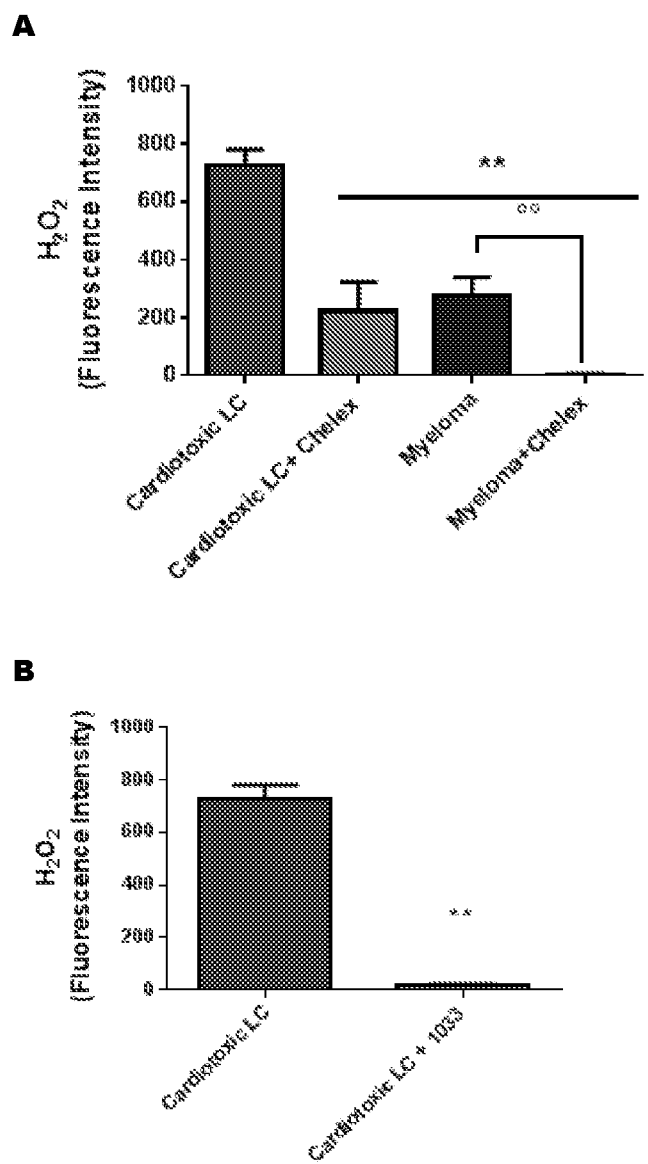
FIG. 2 provides graphical representations of the $H_2O_2$ produced by H7-BJ cardiotoxic LC and MM2-BJ myeloma incubated at room temperature with 50 μM Chelex® resin (A) or H7-BJ cardiotoxic LC incubated at room temperature with or without 2 nM 5,7-dichloro-8-hydroxy-2-(dimethylaminomethyl)quinoline (1033), (B).

H7-BJ protein produced significantly more ROS as determined by hydrogen peroxide concentration, than MM2-BJ and ROS production was significantly attenuated by elution on Chelex® resin (FIG. 2A) or incubation with 2 nM 1033 as shown in FIG. 2B.

Example 4: Effects of Metal Ions

Bristol N2 strain, transgenic CL2070 dvIs70 Is[hsp-16.2:: gfp; rol-6(su1006)], CF1553 muls84 [(pAD76) sod-3p:: GFP+rol-6] and TJ356, zls356Is[daf-16::daf-16-gfp; rol-6] were obtained from the *Caenorhabditis elegans* Genetic Center (CGC, University of Minnesota, USA) and propagated at 20° C. on solid Nematode Growth Medium (NGM) seeded with *E. coli* OP50 (from CGC) for food. The effect of LC on pharyngeal behaviour was investigated (Diomede et al. 2014). Briefly, ancestral N2 and transgenic CL2070, TJ356 and CF1553 worms were incubated with 100 μg/mL LC listed in Table 1A (100 worms/100 μL) in 5 mM PBS, pH 7.4. Control worms were incubated with 5 mM PBS, pH 7.4 (Vehicle) only. After 2 h of incubation on orbital shaking, worms were transferred onto NGM plates seeded with OP50 *E. coli*. The pharyngeal pumping rate, measured by counting the number of times the terminal bulb of the pharynx contracted over a 1-minute interval, was scored 20 h later. Experiments were also performed by feeding worms for 2 h with 100 μg/mL of H6-BJ, H7-BJ, H18-BJ, MM2-BJ, MM4-BJ or MM7-BJ alone or with 125 μM copper (as $CuSO_4$).

Figure 3:
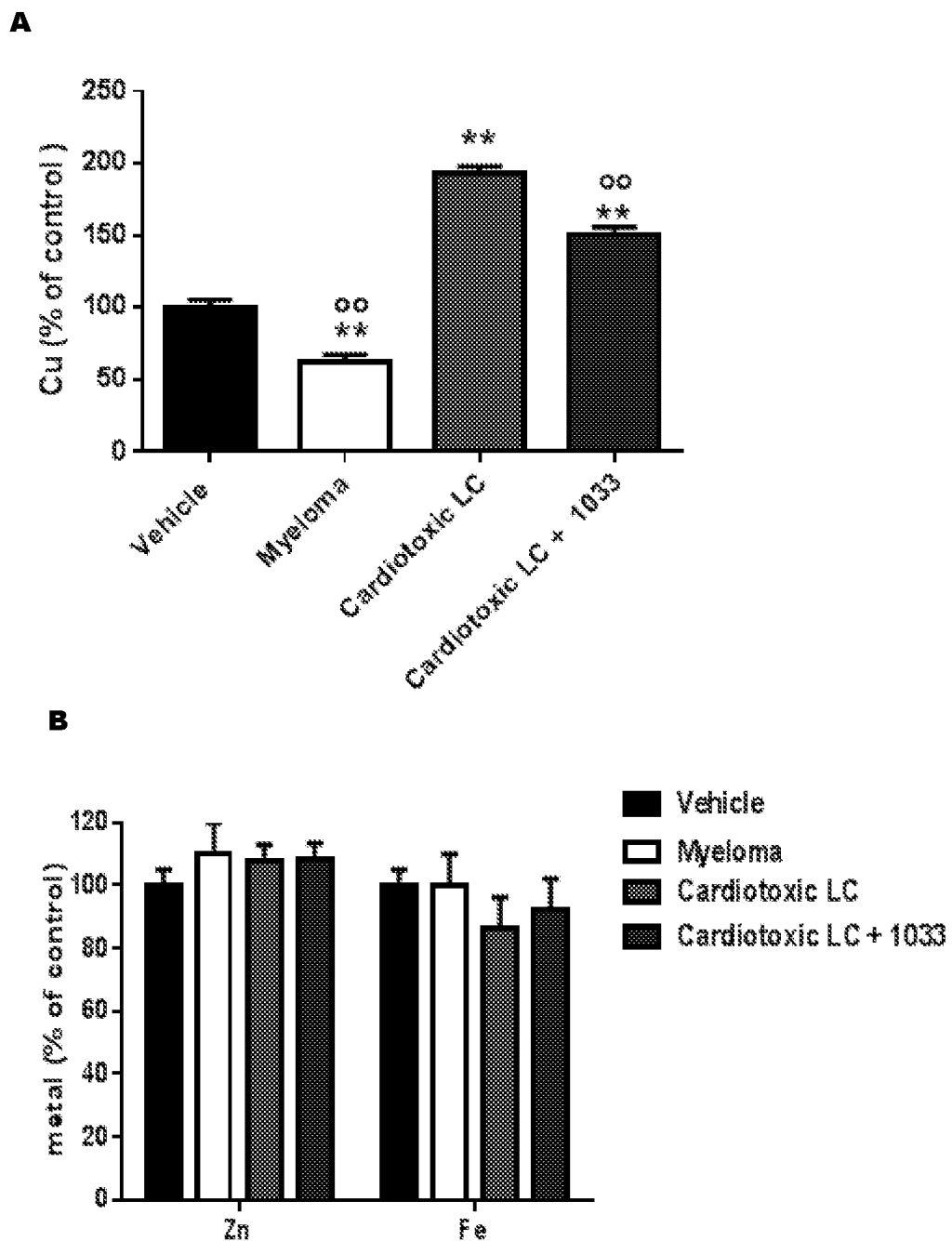
FIG. 3 provides graphical representations of endogenous metal levels and the effects of added copper on *C. elegans* pharyngeal function. Worms fed with 100 μg/mL MM2-BJ (myeloma), 100 μg/mL cardiotoxic LC H7-BJ, cardiotoxic LC+ 2 nM 1033, or metal free water (vehicle) were analysed for the amount of endogenous Cu (A), Zn and Fe (B). The addition of 125 μM copper showed a worsening of pharyngeal dysfunction induced by cardiotoxic LC as demonstrated by the terminal bulb pharyngeal pumping rate (C).
Figure 3:
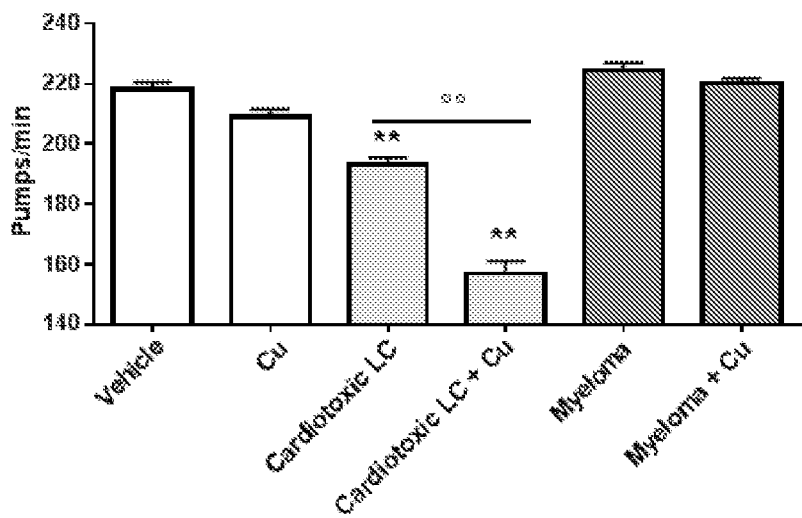

The results are shown in FIGS. 3A and 3B. Feeding of *C. elegans* with cardiotoxic LC, but not myeloma protein, resulted in an increase in endogenous copper levels, whereas zinc and iron levels were not significantly altered. When 125 μM copper was added to the cardiotoxic LC protein solution, a worsening of the pharyngeal dysfunction induced by H7-BJ was observed, whereas the pumping rate of *C. elegans* fed MM2-BJ protein was unaffected by the dose of copper (FIG. 3C).

Example 5: Effects of Metal Chelating Compounds

Figure 4:
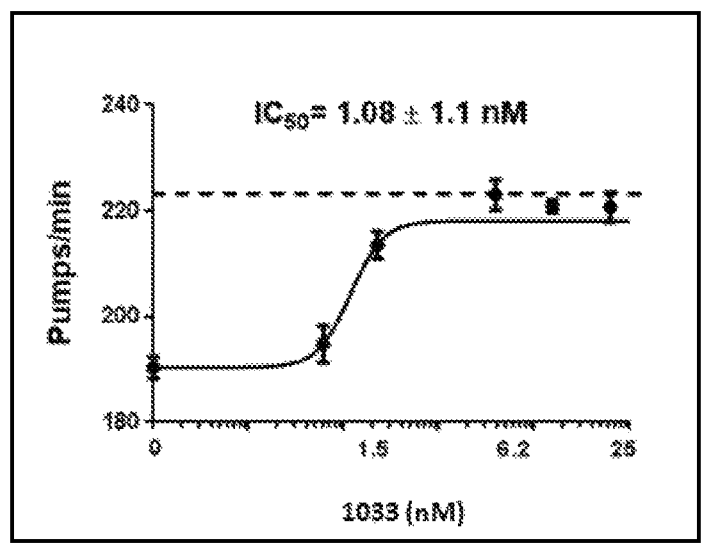
FIG. 4 shows the (A) dose-response effect of 1033 on LC-induced pharyngeal dysfunction. Worms were fed for 2 h with 100 μg/mL H7-BJ in the absence or presence of 0-25 nM 1033. Control worms received vehicle alone (dotted line). Each value is the mean±SE, n=30. $IC_{50}$±SD is reported, p<0.01 Student's t test. (B) Images obtained from the overlay of a contrast phase and MitoSOX fluorescence (arrows). Scale bar 50 μm. (C) The effects of cardiotoxic LC, 1033, cardotoxic LC+1033, $H_2O_2$ and $H_2O_2$+1033 on pharyngeal function. (D) The effects of Chelex® and EDTA on LC induced pharyngeal dysfunction.
Figure 4:
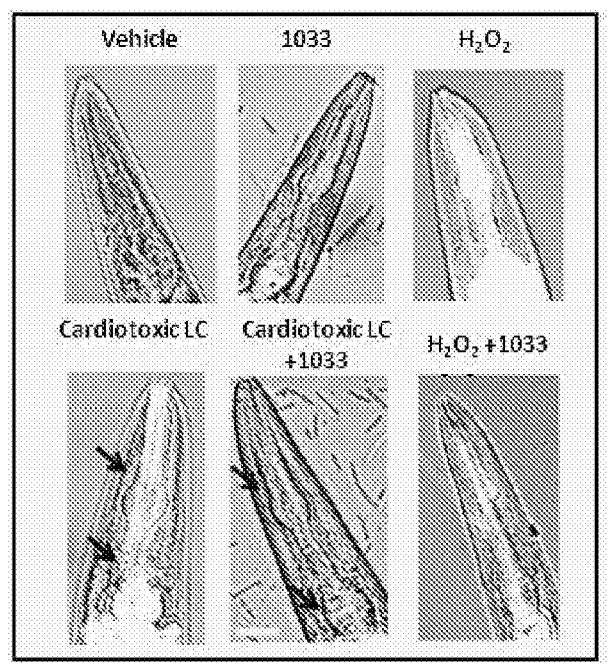
Figure 4:
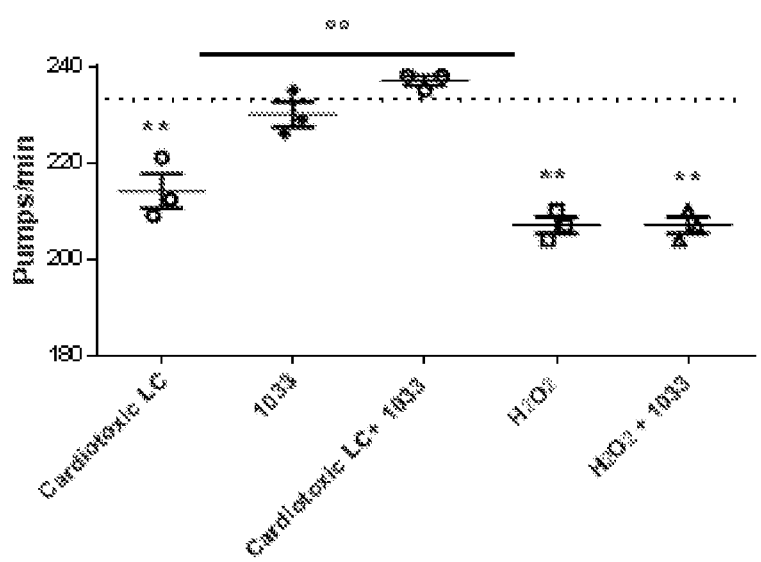
Figure 4:
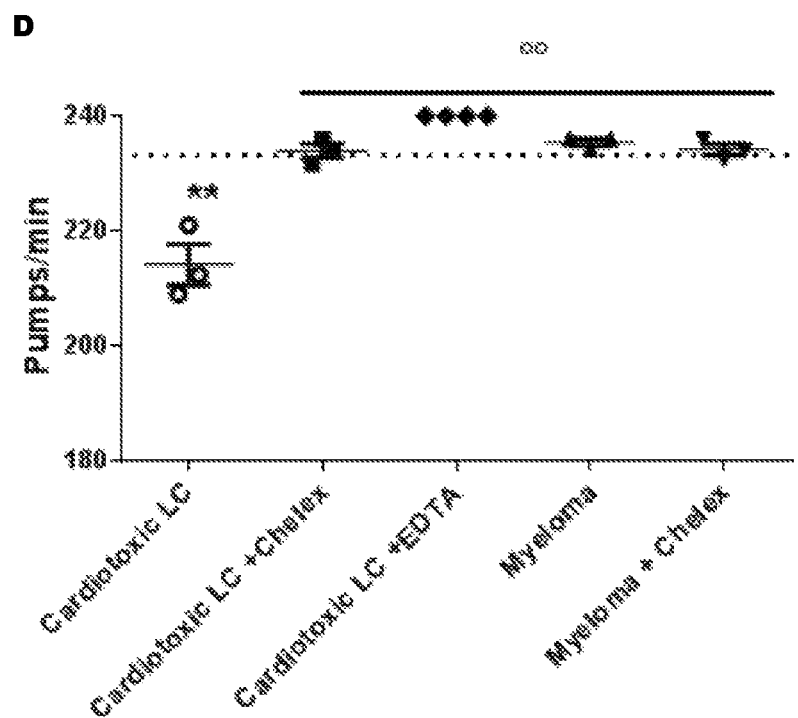

The experimental conditions of Example 4 were repeated with cardiotoxic LC H7-BJ with or without 1033, Chelex® resin or EDTA as well as 1033, $H_2O_2$ and $H_2O_2$ together with 1033. Their effect in counteracting the pharyngeal dysfunction caused by cardiotoxic LC was dose-dependent, 1033 having an $IC_{50}$: 1.08±1.1 nM (FIG. 4A). An optimal concentration of 2 nM for 1033: a dose level that counteracted $H_2O_2$ production (FIG. 2B) and completely abolished the pharyngeal impairment caused by all cardiotoxic LC under investigation (FIGS. 4B and 4C and 4D). 1033 counteracted the cardiotoxic LC-induced elevation of copper levels in worms (FIG. 3A), without affecting the levels of iron or zinc (FIG. 3B). 1033 did not counteract pharyngeal toxicity induced by exposure to exogenous $H_2O_2$ (FIGS. 4B and 4C), but did prevent the increase in exogenous $H_2O_2$ generation caused by H7-BJ (FIG. 2B), indicating that its protective effect against cardiotoxic LC is not related to a general anti-oxidant activity. 1033 alone did not affect the pumping rate (FIG. 4C), nor the increase of pharyngeal mitochondrial oxygen burden. Metal chelation did not affect the secondary structure content and thermostability of LC.

Example 6: Life Span Experiments

N2 worms (100 worms/100 μL), at L3 larval stage, were fed for 2 h 100 μg/mL of H7-BJ alone or with 2 nM 1033. Worms were then transferred onto fresh NGM plates seeded with *E. coli* in the presence of the same drug concentration. Control worms were exposed, under the same conditions, to vehicle alone. After 20 h nematodes were transferred to fresh NGM plates seeded with bacteria and the number of live worms was scored (considered as day 0). To avoid overlapping generations, the worms were then transferred every day, in the absence of fluorodeoxyuridine, until they stopped laying eggs. To test the effect of repeated administration of 1033, worms were fed for 2 h 100 μg/mL of H7-BJ and 2 nM 1033 and then transferred onto fresh NGM plates seeded with *E. coli* in the presence of the same drug concentration. Then nematodes were transferred every day, in a new NGM plate in the presence of freshly dissolved 2 nM 1033. The number of live worms was determined for each consecutive day until all worms were dead.

Figure 5:
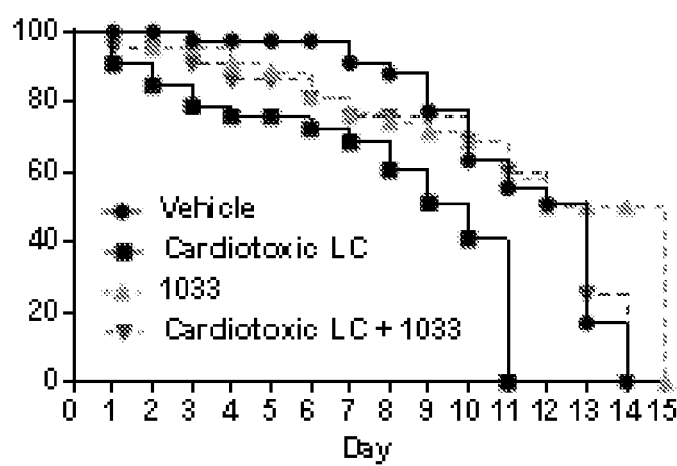
FIG. 5 is a Kaplan-Meier Survival Curve showing the increase in survival induced by 1033, n=30 worms per group; 3 independent experiments.

The exposure of *C. elegans* to cardiotoxic LC significantly reduced their lifespan (median survival: 13 days and 9 days for vehicle- and H7-BJ-fed worms, respectively, p=0.0001, Log-rank test) (FIG. 5). Administration of 2 nM/day 1033 significantly prolonged the survival of cardiotoxic LC-treated worms, restoring their natural lifespan (median survival: 13 days for H7-BJ+2 nM/day 1033 (p=0.025 vs. H7-BJ)) (FIG. 5). No protective effect was observed when a single dose of 1033 at 2 nM was administered, likely due to solubility problems rather than stability issues of the drug. In fact 1033 is extremely stable under physiological conditions and in a variety of standard solvents. Overall, these findings indicated that the disruption of metal ion homeostasis was implicated in the ability of cardiotoxic LC to generate ROS.

Example 7: Modulation of the FOXO Signaling Pathway

DAF-16::green fluorescent protein (GFP) nuclear translocation was evaluated in TJ356 nematodes. Pharyngeal expression of HSP-16.2::GFP and SOD-3::GFP was determined in CL2070 and CF1553 worms, respectively. Young adult nematodes were incubated for 2 h at 20° C. with 100 μg/mL H7-BJ or MM2-BJ (100 worms/100 μL) in 10 mM PBS, pH 7.4, in the absence or presence of 2 nM 1033, 50 μM tetracycline (TETRA) and 5 mM N-acetyl cysteine (NAC). Control worms were incubated with 10 mM PBS, pH 7.4, (vehicle) or drugs alone. After 2-20 h, nematodes were paralyzed by adding 1 mM levamisole, transferred to tubes containing 1 mL of M9 plus 1 mM levamisole, centrifuged at 2000 g for 5 min at room temperature, and fixed in 4% Paraformaldehyde in 5 mM PBS, pH 7.4, for 24 h at 4° C. Nuclear translocation of DAF-16 was visualized with an inverted fluorescent microscope (IX-71 Olympus) equipped with a CDD camera. Organisms were scored as positive for nuclear localization when green foci were observed throughout the entire body from head to tail and as cytosolic when DAF-16::GFP was diffuse. The number of worms with each level of translocation were counted (at least 100 worms/condition). The assay was repeated at least four times. For HSP-16.2 and SOD-3 GFP-expression in the pharynx of worms images were acquired using the same exposure settings. Average pixel intensity values were calculated by sampling images of different animals. Mean pixel intensity for each experimental group was calculated using Cell-F software (Olympus). For each experiment at least 25 worms were examined for each strain/condition. Each experiment was repeated at least three times.

Figure 6:
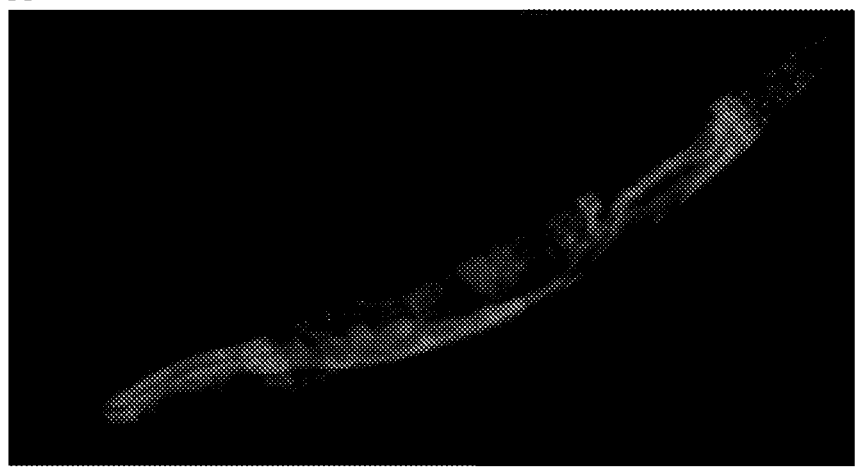
FIG. 6 shows the effect of cardiotoxic LC on the DAF-16 translocation from cytoplasm to nucleus in TJ356 transgenic worms. (A) Image of DAF-16::GFP expression in control vehicle-fed and (B) cardiotoxic LC-fed worms (100 μg/mL H7-BJ for 2 h). (C-D) The subcellular distribution of DAF-16 expression in worms fed 2 h: vehicle, 100 μg/mL H7-BJ with or without 2 nM 1033, 50 μM tetracycline (TETRA) or 5 mM N-acetyl cysteine (NAC). According to DAF-16 localization worms were divided into two phenotypes including "cytosolic" and "nuclear". The percentage of DAF-16 localization in respect to vehicle fed worms was calculated based on 3 experiments, N=100. Mean±SE. **p<0.01 vs. vehicle, °p<0.05 and °°p<0.01 vs. cardiotoxic LC, one-way ANOVA and Bonferroni's post hoc test. (E/F) Transgenic worms were fed with 1 mM $H_2O_2$ for 30 minutes as a positive control. DAF-16::GFP distribution (E) and HSP-16.2 and SOD-3 expression visualized by GFP-fluorescence (F).
Figure 6:
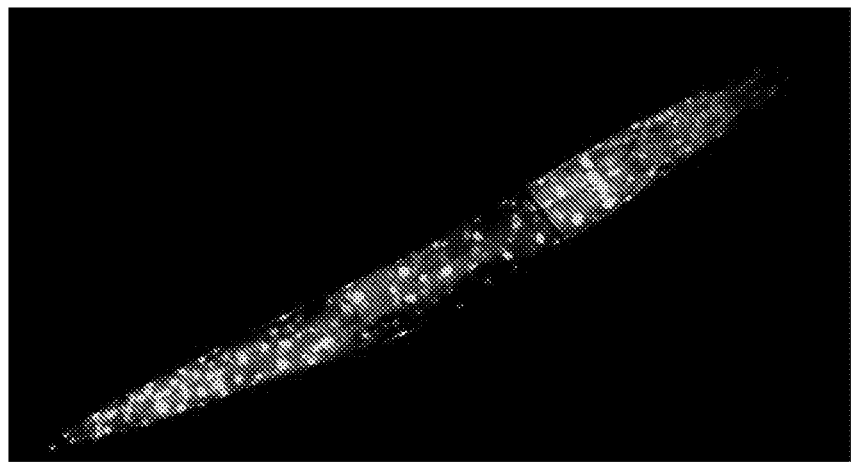
Figure 6:
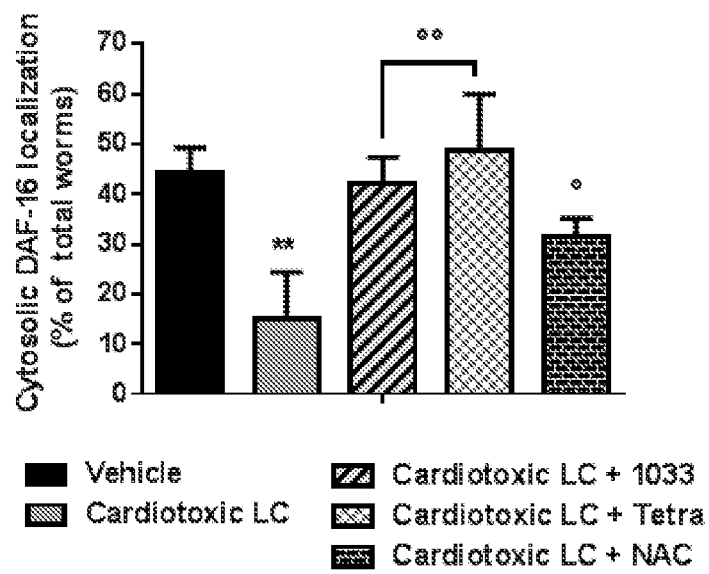
Figure 6:
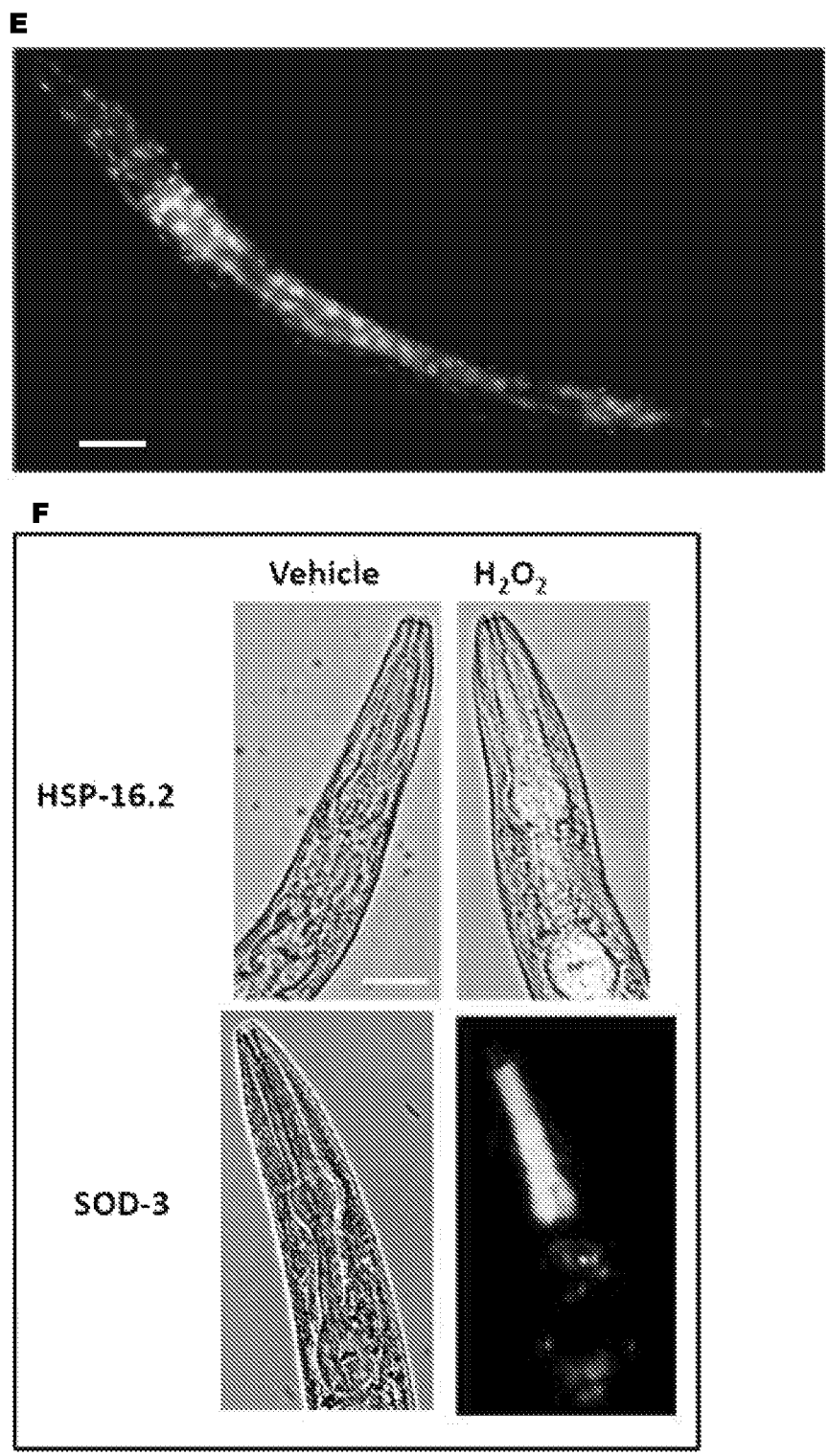

In *C. elegans* an increase in ROS levels can result in the activation of the Insulin/Insulin Growth Factor-1 signalling pathway (Back et al., 2012; Hartwig et al., 2009), driving the regulation of the FOXO/DAF-16, which actively controls diverse target genes involved in oxidative stress resistance and survival (Mukhoposdhyay et al., 2006). It was observed that ROS generated by cardiotoxic LC act as signalling molecules modulating the FOXO signalling pathway. Under basal conditions (vehicle fed worms), DAF-16 was mainly localized in the cytosol of transgenic TJ356 *C. elegans* nematodes expressing GFP under control of daf-16 promoter (Hartwig et al., 2009) (FIGS. 6A and 6C). The administration of H7-BJ caused a significant increase of the nuclear translocation of DAF-16, detectable as the appearance of condensed green foci in the bodies of the worms (FIGS. 6B and 6D). A similar effect was observed when nematodes were fed $H_2O_2$ as a positive control (FIGS. 6E and 6F). 1033 counteracted the activation of DAF-16 induced by the cardiotoxic LC (FIGS. 6C and 6D). A similar effect was not observed when H7-BJ was administered together with an antioxidant prototypic compound (5 mM NAC) (FIGS. 6C and 6D). On the contrary TETRA (50 μM), a known antibiotic which has also antioxidant and metal ion chelator activity (Chin and Lack, 1975; Stailova et. al., 2013), counteracted DAF-16 activation induced by cardiotoxic LC (FIGS. 6C and 6D).

Figure 7:
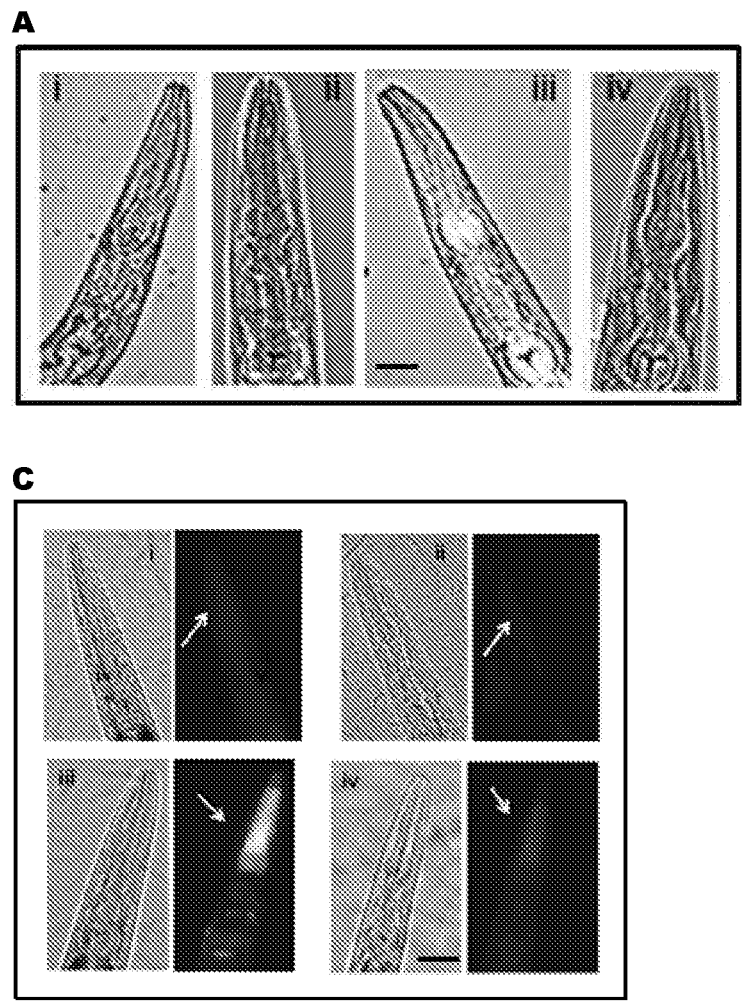
FIG. 7 shows that cardiotoxic LC induces the pharyngeal expression of HSP-16.2 and SOD-3. Transgenic worms were fed for 2 h with: Vehicle (i, 5 mM PBS, pH 7.4) 100 μg/mL MM2-BJ (ii, Myeloma), 100 μg/mL H7-BJ (iii, Cardiotoxic LC), or 2 nM 1033 (iv, Cardiotoxic LC+ 1033). (A) Images of the HSP-16.2 expression as overlays of GFP-fluorescence and light microscopy in CL2070 transgenic worms. Scale bar 50 μm. (C) Images of SOD-3 expression as GFP-fluorescence (arrows) in CF1553 transgenic worms. Scale bar 50 μm. Quantified GFP intensity in (B) CL2070 and (D) CF1553 worms in response to treatments. Fluorescence intensity in each group was calculated as mean grey value+ SE based on 3 experiments, N=25. **p<0.01 vs. Vehicle and °p<0.05 and °°p<0.01 vs. Cardiotoxic LC, one-way ANOVA and Bonferroni's post hoc test.
Figure 7:
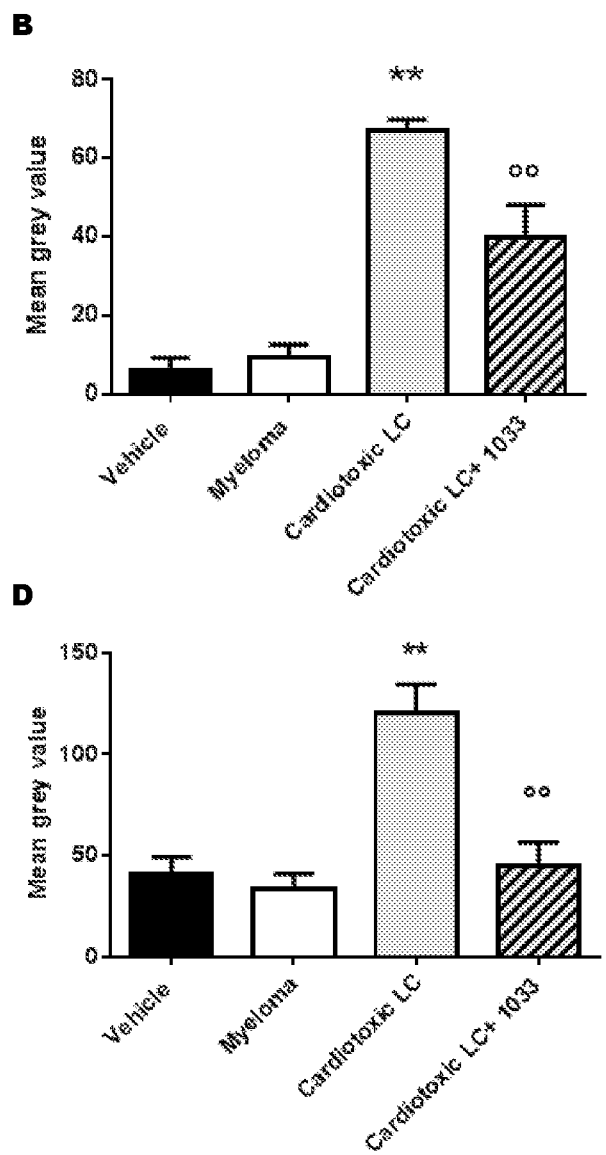

The adaptive responses of the antioxidant defense system were then evaluated. In particular, activation of the expression of small HSP-16.2, which can act as a ROS-sensor and also affect the lifespan of worms (Hartwig et al., 2009), and the activity of the antioxidant enzyme manganese superoxide dismutase SOD-3 were determined using transgenic CL2070 (Hartwig et al., 2009) and CF1553 (Anbalagan et al., 2012) worms, expressing GFP control of hsp-16.2 or sod-3 promoter, respectively. H7-BJ, but not MM2-BJ, caused a significant increase in HSP-16.2 (FIG. 7A, B) as well as SOD-3 expression (FIG. 7C, D) in the pharynx of nematodes, similarly to that observed with $H_2O_2$. In contrast, exposure to 1033 significantly reduced the LC-induced HSP-16.2 and SOD-3 protein expression, as indicated by the absence of GFP signal in the pharynx of CL2070 and CF1553 worms, respectively (FIG. 7).

Overall these results indicated that cardiotoxic LC, by means of metal ion-mediated ROS production and consequent FOXO/DAF-1 pathway activation, stimulate genes involved in the control of the oxidative stress response and lifespan, and that LC co-incubation with metal chelating compounds, such as 1033, abolished the worm stress response.

Example 8: Cardiotoxic LC Damage in Mitochondria Vs ROS Generation

Whether ROS produced by cardiotoxic LC caused alterations in pharyngeal sub-cellular compartments, particularly mitochondria, which play a vital role in providing energy for contractile activity was investigated.

N2 worms fed 100 μg/mL H6-BJ, H7-BJ, MM2-BJ or MM4-BJ LC (100 worms/100 μL) in 5 mM PBS, pH 7.4, alone or with: 5 mM NAC in 5 mM PBS, pH 7.4; 50 μM TETRA in 5 mM PBS, pH 7.4; or 2 nM 1033. Control worms were incubated with vehicle alone (Vehicle) only. After 2 h of incubation on orbital shaking, worms were transferred onto NGM plates seeded with OP50 *E. coli* in the presence of the same drug concentration. Twenty 20 h later, *C. elegans* were picked, washed in 10 mM PBS, pH 7.4, and fixed with 2% glutaraldehyde in 0.12 M phosphate buffer, pH 7.4. Worms were then cut open at the level of second bulb of the pharynx, to improve access of the fixative. After post-fixation at room temperature overnight, samples were incubated in a solution of 1% $OsO_4$ 1.5% ferrocyanide in 0.12 M cacodylate buffer (ferrocyanide-reduced $OsO_4$) at room temperature for 1 h, then 0.3% thiocarbohydrazide in $H_2O$ for 5 min, and finally 2% $OsO_4$ in 0.12 M cacodylate buffer for 1 h. *C. elegans* pharynx was then placed into 2% agarose gel and small cubes were cut and dehydrated in graded series of ethanol for 10 min each, cleared in propylene oxide and embedded in Epoxy medium (Epon 812 Fluka) and polymerized at 60° C. for 72 h. From each sample, one semithin (1 μm) section was cut with a Leica EM UC6 ultramicrotome and mounted on glass slides for light microscopic inspection. Ultrathin (60-80 nm thick) sections of areas of interest were obtained, counterstained with uranyl acetate and lead citrate, and examined with an Energy Filter Transmission Electron Microscope (EFTEM, ZEISS LIBRA® 120) equipped with a YAG scintillator slow scan CCD camera.

Specimens of human myocardial tissue (Table 1B) were fixed with 2.5% glutaraldehyde in 0.2 M cacodylate buffer, pH 7.3 for 2 h, and post-fixed in 1% osmium tetroxide in the same buffer. They were then dehydrated in a graded series of ethyl alcohols and embedded in epoxy resin. Ultrathin sections (60-80 nm thick) were cut, mounted on nickel grids and stained with 5% uranyl acetate and lead citrate (Reynold's solution). A minimum of 5 sections for each patient were observed with a Philips CM12 transmission electron microscope. Sections were then processed for post-embedding immunogold as previously described (Fernandez de Larrea, et al., 2014). Briefly, enzymatic predigestion (0.05% trypsin in Tris buffer with 0.05% $CaCl_2$, 37° C., 15 min) to unmask antigenic epitopes was performed. The sections were then rinsed in 0.05 M Tris/HCl buffer, pH 7.3, incubated with either 1:20 normal goat serum or 1% egg albumin for 15 min at room temperature. The sections were incubated overnight at 4° C. with polyclonal anti-λ LC antibody (dilution 1:50, Dako, Agilent Technologies, CA, USA), then incubated for 1 h at room temperature with protein-A (dilution 1:20), conjugated to 15 nm colloidal gold particles (British Biocell International, UK).

Specificity of immunoreactions was verified using either normal goat serum or egg albumin as primary antibody.

Figure 8:
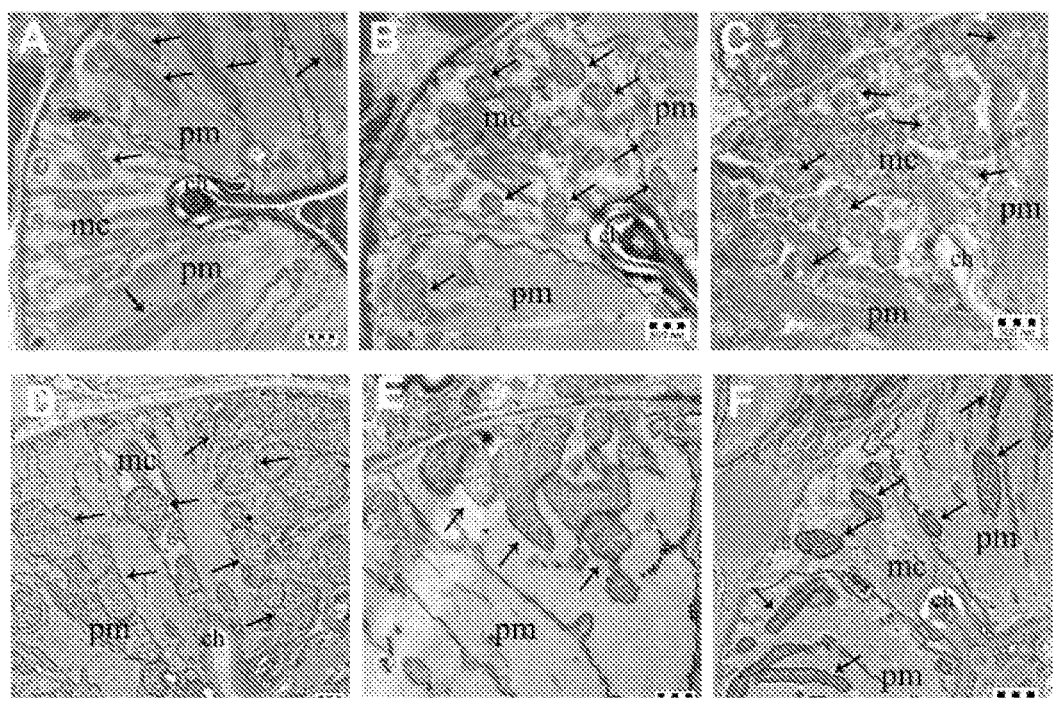
FIG. 8 shows that cardiotoxic LC severely disrupts *C. elegans* pharyngeal ultrastructure. Representative images of worm's pharynx obtained from the ultrastructural analysis by transmission electron microscopy (TEM) in *C. elegans* fed for 2 h with: (A) Vehicle, (B) Myeloma protein (MM2-BJ), (C) Cardiotoxic LC (H7-BJ) alone or with (D) 2 nM 1033, (E) 50 μM tetracycline or (F) 5 mM N-acetyl cysteine. Images showed two pharyngeal muscles (pm) with their mitochondria (arrowheads) separated by a marginal cell (mc) and its mitochondria (arrows), placed at the corner of the pharyngeal channel (ch). Pharyngeal muscles of worms fed Cardiotoxic LC resulted in a damage to mitochondria which exhibited a clustering pattern and irregular shape, swelling and massive disruption of the internal components (i.e. cristae). Marginal cells, which contain many mitochondria due to their active role in contractile motor function, were seriously compromised and myofilaments connected to the marginal cells, which were perfectly aligned in vehicle-fed worms, were deranged.
Figure 9:
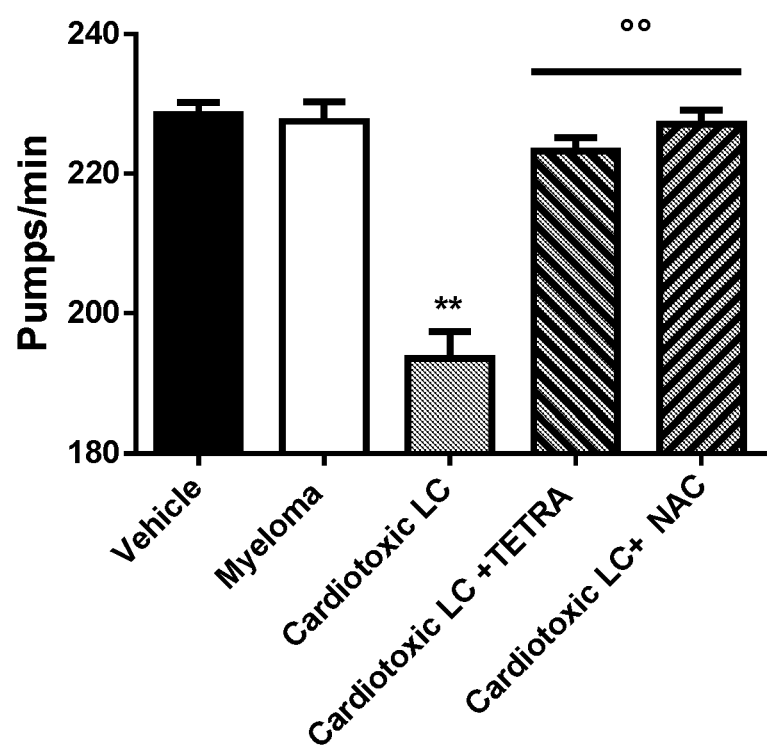
FIG. 9 shows the protective effect of tetracycline (TETRA) and N-acetyl-cysteine (NAC) on the pharyngeal pumping dysfunction caused by cardiotoxic LC. MM2-BJ (Myeloma) and H7-BJ (Cardiotoxic LC) and in 5 mM PBS, pH 7.4, were administered to worms (100 worms/100 μL) at 100 μg/mL alone or with 50 μM TETRA or 5 mM NAC. Control worms received vehicle alone (Vehicle). After incubation for 2 h in the absence of OP50 *E. coli*, worms were plated on NGM plates seeded with bacteria. Pharyngeal pumping was evaluated 20 h after plating and expressed as pumps/minute. **p<0.01 vs. vehicle and °°p<0.01 vs. Cardiotoxic LC, according to one-way ANOVA and Bonferroni's post hoc test.

Transmission electron microscopy (TEM) analyses showed that the pharyngeal muscles of worms fed H7-BJ, but not MM2-BJ, resulted in profound alteration to the pharyngeal ultrastructure and caused mitochondrial damage compared with vehicle treated nematodes (FIG. 8 A-C). Similar features were observed when worms were fed H6-BJ, a cardiac amyloid LC derived from an unrelated germline gene, demonstrating that the observed functional and structural effects were strictly dependent on features that are intrinsic to cardiac LC, with no restriction to a particular germline gene or set of genes.

Furthermore, 1033, as well as TETRA and NAC, were capable of neutralizing the ROS generation and pumping dysfunction caused by cardiotoxic LC (Diomede et al., 2014) (FIGS. 8D-F and FIG. 9). These findings indicated that the specific ability of cardiotoxic LC to damage subcellular pharyngeal structures, particularly mitochondria, derived from their ability to generate ROS. In addition, metal chelating compounds were able to block ROS production and anti-oxidant drugs which prevent oxidative damage defended against cardiac LC-induced tissue injury.

Figure 10:
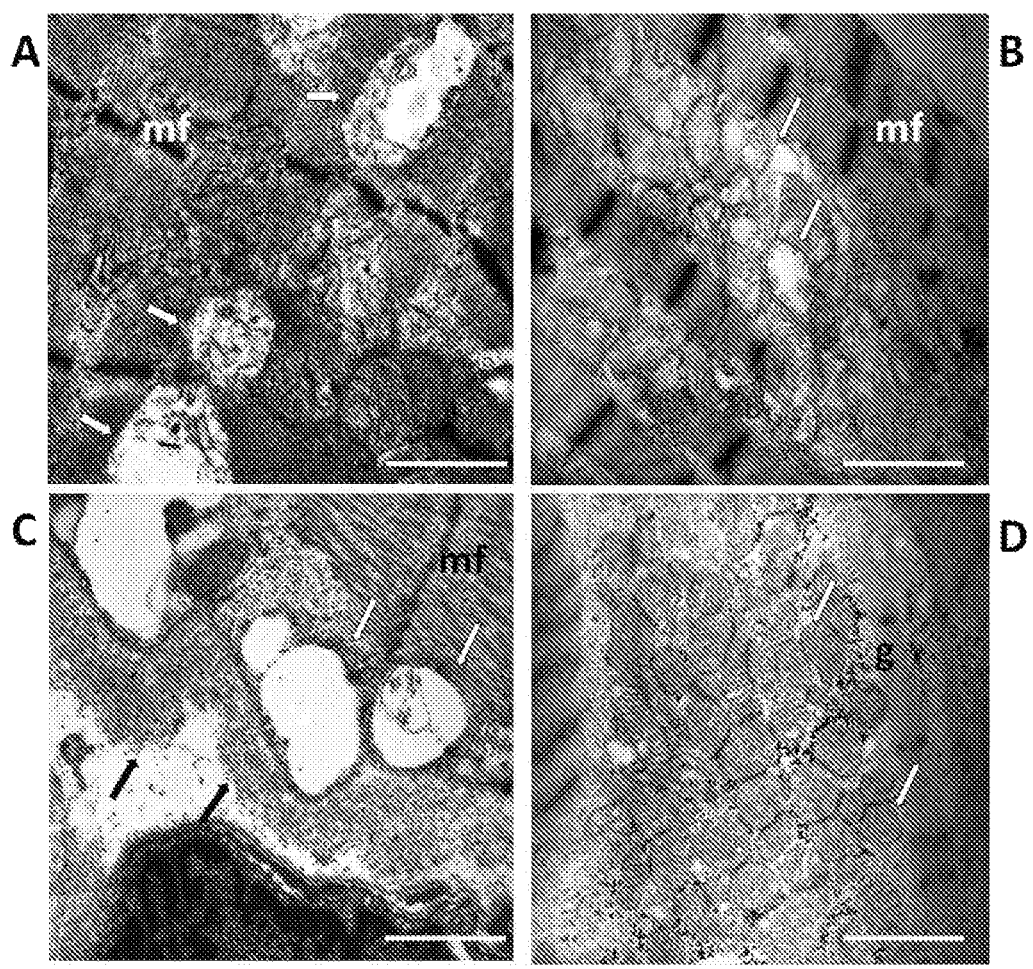
FIG. 10 shows mitochondrial damage in heart muscle tissue of cardiac AL patients. Ultrastructural details from representative transmission electron microscopy (TEM) images of endomyocardial biopsies from severe cardiac amyloid AL patients (A-C) and a patient affected by dilatative cardiomyopathy (D). Although myocardial fibers (mf) are relatively well preserved in AL patients (A-C), most mitochondria (white arrows) show remarkable alterations with enlarged size and disruption (A) or total loss of cristae (B-C). LC were identified by post embedding immunogold staining with 15 nm gold-conjugated protein A (black arrows) in the interstitium and along the basement membrane of a myocardial fiber. (D) The myocardium of a patient with non-amyloid cardiomyopathy shows well preserved mitochondria (white arrows) and glycogen deposits (g). Uranyl acetate, lead citrate. Bar: 1 μm.

Whether the subcellular alterations observed in worms were comparable to damage caused by cardiac LC in human heart tissue was tested. To this end, endomyocardial biopsies from AL patients with advanced cardiac dysfunction (see Table 1B for clinical characteristics) were processed promptly for TEM. Similar to worms exposed to cardiac LC (FIG. 8C), most human mitochondria showed dramatic structural derangement (FIG. 10A-C). In contrast, endomyocardial biopsies from subjects who had undergone heart transplantation for primary dilated cardiomyopathy (used as controls for disease and severity of heart dysfunction) showed fully preserved mitochondria and only scattered mitochondria with minor alterations (FIG. 10D).

These results, resembling those reported by Guan et al. 2014, lend support to the validity of the nematode model and reinforce the rationale of its use for designing and testing of new therapeutic approaches.

Example 9: Cardiotoxic LC Administered Prior to Antioxidant

Figure 11:
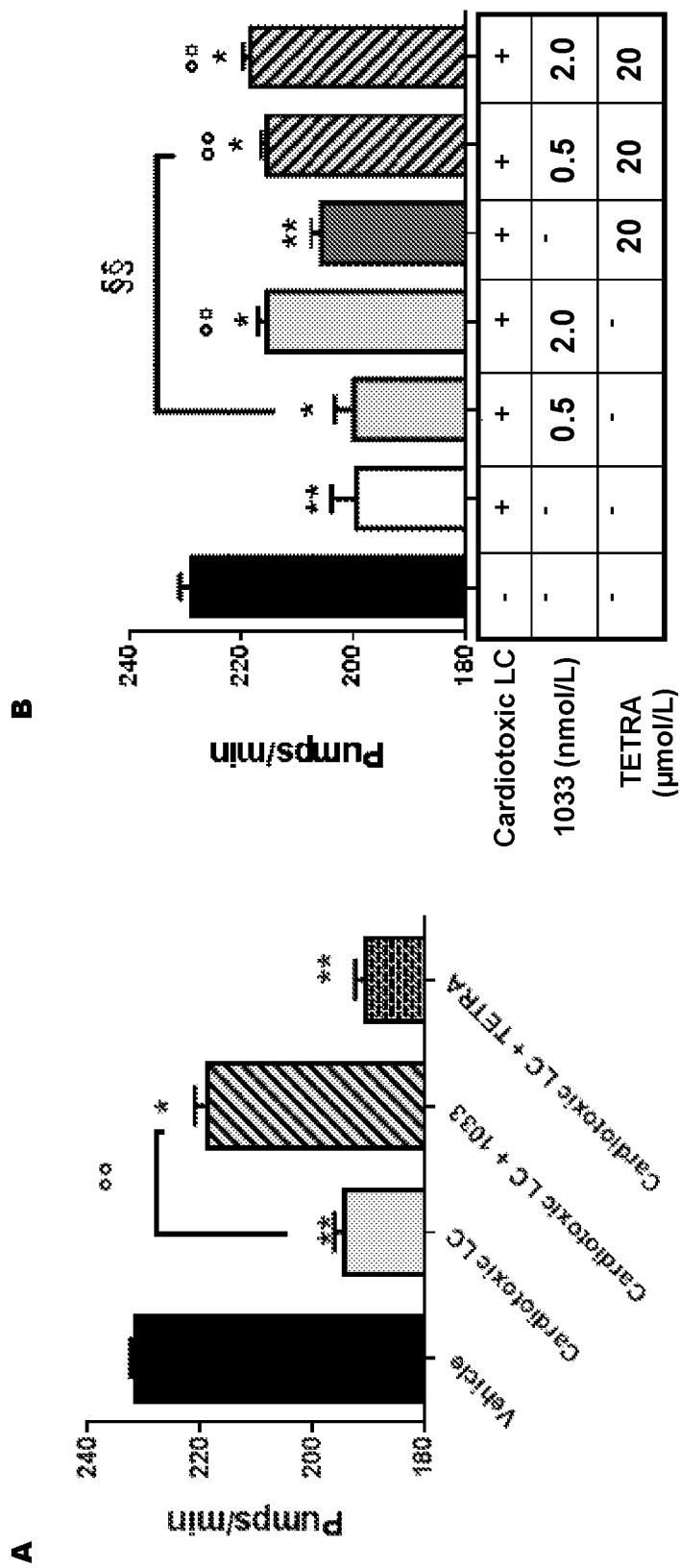
FIG. 11 shows a synergistic beneficial effect of 1033 and tetracycline. Pharyngeal performance of worms fed 100 μg/mL H7-BJ (Cardiotoxic LC) for 1.5 h and then treated for 30 min with 20 M tetracycline (TETRA), 0.5-2 nM 1033 alone or together with 20 μM TETRA. Control worms fed vehicle alone. **p<0.001, *p<0.005 vs. vehicle, °°p<0.001 vs. Cardiotoxic LC, one-way ANOVA and Bonferroni's post hoc test. §§ p<0.01 significant interaction vs. worms fed Cardiotoxic LC+ 0.5 nM 1033, two-ways ANOVA and Bonferroni's post hoc test.

To reflect circumstances most likely encountered in the clinic drugs were administered to worms when the pharynx was already damaged by cardiotoxic LC. Nematodes were fed H7-BJ for 1.5 h to generate pharyngeal dysfunction comparable to that obtained when the LC was administered for 2 h (FIG. 11A). Then drugs were administered for 30 min and the pumping rate was scored. At 2 nM 1033 was capable of restoring normal pharyngeal function caused by H7-BJ, whereas 20 µM TETRA (dose corresponding to the $IC_{50}$ value) were ineffective (FIG. 11A).

Example 10: Synergistic Effect of TETRA and 1033

Feeding experiments in which nematodes were fed H7-BJ for 1.5 h to generate pharangeal dysfunction, subsequently 20 µM TETRA, 0.5 nM 1033, 2 nM 1033, 20 µM TETRA and 0.5 nM 1033.

The results are shown in FIG. 11B. 20 µM TETRA had minimal effects on restoring pharangeal function and 0.5 nM 1033 had no effect on restoring pharangeal function. 2 nM 1033 alone and 2 nM 1033 combined with 20 µM TETRA provided similar results perhaps because maximal recovery of pharangeal function (53%) was already obtained by the 2 nM 1033.

However, 20 µM TETRA together with 0.5 nM 1033, an ineffective concentration provided a synergistic effect. These data suggest that the combined administration of low doses of 1033 and TETRA may represent an innovative pharmacological approach to break the vicious cycle of oxidative stress induced by cardiotoxic LC.

REFERENCES

Anbalagan C, Lafayette I, Antoniou-Kourounioti M, et al. Transgenic nematodes as biosensors for metal stress in soil pore water samples. *Ecotoxicology.* 2012; 21(2):439-455.

Back P, Braeckman B P, Matthijssens F. ROS in aging *Caenorhabditis elegans*: damage or signaling? *Oxid Med Cell Longev.* 2012; 2012:608478.

Chin T F, Lach J L. Drug diffusion and bioavailability: tetracycline metallic chelation. *Am J Hosp Pharm.* 1975; 32(6):625-629.

Diomede L, Rognoni P, Lavatelli F, et al. A *Caenorhabditis elegans*-based assay recognizes immunoglobulin light chains causing heart amyloidosis. *Blood.* 2014; 123(23): 3543-3552.

Fernandez de Larrea C, Verga L, Morbini P, et al. A practical approach to the diagnosis of systemic amyloidoses. *Blood.* 2015; 125(14):2239-2244.

Gertz M A, Comenzo R, Falk R H, et al. Definition of organ involvement and treatment response in immunoglobulin light chain amyloidosis (AL): a consensus opinion from the 10th International Symposium on Amyloid and Amyloidosis, Tours, France, 18-22 Apr. 2004. *Am J Hematol.* 2005; 79(4):319-328.

Guan J, Mishra S, Qiu Y, et al. Lysosomal dysfunction and impaired autophagy underlie the pathogenesis of amyloidogenic light chain-mediated cardiotoxicity. *EMBO Mol Med.* 2014; 6(11):1493-1507.

Hartwig K, Heidler T, Moch J, Daniel H, Wenzel U. Feeding a ROS-generator to *Caenorhabditis elegans* leads to increased expression of small heat shock protein HSP-16.2 and hormesis. *Genes Nutr.* 2009; 4(1):59-67.

Liang S, et al., Novel fluorinated 8-hydroxyquinoline based metal ionophores for exploring the metal hypothesis of Alzheimer's disease. *Med. Chem. Lett.,* 2015, DOI: 10.1021/acsmedchemlett.5b00281.

Merlini G, Bellotti V., Molecular mechanisms of amyloidosis. *N. Engl. J. Med.,* 2003; 349 (6):583-596.

Merlini G, Palladini G., Amyloidosis: is a cure possible? *Ann Oncol.* 2008; 19 Suppl 4:iv63-66.

Mukhopadhyay A, Oh S W, Tissenbaum H A. Worming pathways to and from DAF-16/FOXO. *Exp Gerontol.* 2006; 41(10):928-934.

Perfetti V, Sassano M, Ubbiali P, et al. Inverse polymerase chain reaction for cloning complete human immunoglobulin variable regions and leaders conserving the original sequence. *Anal Biochem.* 1996; 239(1):107-109.

Rognoni P, Lavatelli F, Casarini S, et al. A strategy for synthesis of pathogenic human immunoglobulin free light chains in *E. coli. PLoS One.* 2013; 8(9):e76022.

Stoilova T, Colombo L, Forloni G, Tagliavini F, Salmona M. A new face for old antibiotics: tetracyclines in treatment of amyloidoses. *J Med Chem.* 2013; 56(15):5987-6006.

Wechalekar A D, Schonland S O, Kastritis E., et al., A European collaborative study of treatment outcomes in 346 patients with cardiac stage III AL amyloidosis. *Blood.* 2013; 121(17): 3420-3427.

The invention claimed is:

1. A method of treating immunoglobulin light chain amyloidosis in a subject in need thereof comprising administering a compound of formula (I):

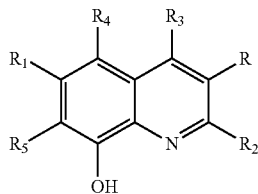

(1)

wherein
R, $R^1$ and $R^3$ are the same or different and are each independently selected from hydrogen, —$C_{1-3}$ alkyl, —$C_{2-3}$ alkenyl, —$C_{2-3}$ alkynyl, —$CF_3$, —$CHF_2$, —$CH_2F$, —$CH_2CF_3$, —$CH_2CF_2H$, —$CH_2CH_2F$, —OH, —$OC_{1-6}$ alkyl, —$OCF_3$, —$OCHF_2$, —$OCH_2F$, —$OCH_2CF_3$, —$OCH_2CHF_2$, —$OCH_2CH_2F$, —$OC_{2-3}$ alkenyl, —$OC_{2-3}$ alkynyl, —$NH_2$, —$NH(C_{1-3}$ alkyl), —$N(C_{1-3}$ alkyl$)_2$, —$SO_2C_{1-6}$ alkyl, —$CO_2H$, —$CO_2C_{1-3}$ alkyl, —$CONH_2$, —$CONH(C_{1-3}$ alkyl), —$CON(C_{1-3}$ alkyl$)_2$, F, Cl and Br;
$R^2$ is selected from —$(CH_2)_m$heterocyclyl, —$(CH_2)_mC(O)R^9$, —$(CH_2)_mCN$, —$(CH_2)_mNR^7R^8$, —CH=$NC_{1-6}$ alkyl, —CH=N—$OR^6$, —CH=N—$NR^{10}R^{11}$, —$SO_2NR^{10}R^{11}$ and —$(CH_2)_mOR^6$;
$R^4$ and $R^5$ are the same or different and are independently selected from F, Cl and I;
$R^6$ is selected from hydrogen, —$C_{1-6}$ alkyl, —$C_{2-6}$ alkenyl, —$C_{2-6}$ alkynyl, —$C_{1-6}$ haloalkyl, aryl and heteroaryl;
$R^7$ and $R^8$ are the same or different and are independently selected from hydrogen, —$C_{1-6}$ alkyl, —$C_{2-6}$ alkenyl, —$C_{2-6}$ alkynyl, —$C_{1-6}$ haloalkyl, —$(CH_2)_m$aryl and —$(CH_2)_m$heterocyclyl, or $R^7$ and $R^8$ taken together form a heterocyclic ring;
$R^9$ is selected from hydrogen, —$C_{1-6}$ alkyl, —$C_{2-6}$ alkenyl, —$C_{2-6}$ alkynyl, —$C_{1-6}$ haloalkyl, —$OR^6$, —$SR^6$, —$NR^7R^8$, aryl and heteroaryl;
$R^{10}$ and $R^{11}$ are the same or different and are independently selected from hydrogen, —$C_{1-6}$ alkyl, —$C_{2-6}$ alkenyl, —$C_{2-6}$ alkynyl, —$C_{1-6}$ haloalkyl, aryl and heteroaryl;
m is 0 or 1;
wherein each alkyl, alkenyl, alkynyl, aryl and heteroaryl group may be optionally substituted;
or a pharmaceutically acceptable salt, hydrate or solvate thereof.

2. The method according to claim 1 wherein the method alleviates or reverses the symptoms of immunoglobulin light chain amyloidosis.

3. The method according to claim 1 wherein the immunoglobulin light chain amyloidosis is cardiac immunoglobulin light chain amyloidosis.

4. A method of treating or alleviating or reversing the symptoms of cardiotoxicity associated with immunoglobulin light chain amyloidosis in a subject in need thereof comprising administering a compound of formula (I):

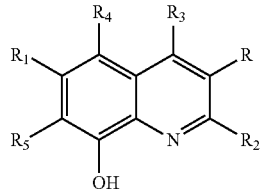

(1)

wherein
R, $R^1$ and $R^3$ are the same or different and are each independently selected from hydrogen, —$C_{1-3}$ alkyl, —$C_{2-3}$ alkenyl, —$C_{2-3}$ alkynyl, —$CF_3$, —$CHF_2$, —$CH_2F$, —$CH_2CF_3$, —$CH_2CF_2H$, —$CH_2CH_2F$, —OH, —$OC_{1-6}$ alkyl, —$OCF_3$, —$OCHF_2$, —$OCH_2F$, —$OCH_2CF_3$, —$OCH_2CHF_2$, —$OCH_2CH_2F$, —$OC_{2-3}$ alkenyl, —$OC_{2-3}$ alkynyl, —$NH_2$, —$NH(C_{1-3}$ alkyl), —$N(C_{1-3}$ alkyl$)_2$, —$SO_2C_{1-6}$ alkyl, —$CO_2H$, —$CO_2C_{1-3}$ alkyl, —$CONH_2$, —$CONH(C_{1-3}$ alkyl), —$CON(C_{1-3}$ alkyl$)_2$, F, Cl and Br;
$R^2$ is selected from —$(CH_2)_m$heterocyclyl, —$(CH_2)_mC(O)R^9$, —$(CH_2)_mCN$, —$(CH_2)_mNR^7R^8$, —CH=$NC_{1-6}$ alkyl, —CH=N—$OR^6$, —CH=N—$NR^{10}R^{11}$, —$SO_2NR^{10}R^{11}$ and —$(CH_2)_mOR^6$;
$R^4$ and $R^5$ are the same or different and are independently selected from F, Cl and I;
$R^6$ is selected from hydrogen, —$C_{1-6}$ alkyl, —$C_{2-6}$ alkenyl, —$C_{2-6}$ alkynyl, —$C_{1-6}$ haloalkyl, aryl and heteroaryl;
$R^7$ and $R^8$ are the same or different and are independently selected from hydrogen, —$C_{1-6}$ alkyl, —$C_{2-6}$ alkenyl, —$C_{2-6}$ alkynyl, —$C_{1-6}$ haloalkyl, —$(CH_2)_m$aryl and —$(CH_2)_m$heterocyclyl, or $R^7$ and $R^8$ taken together form a heterocyclic ring;
$R^9$ is selected from hydrogen, —$C_{1-6}$ alkyl, —$C_{2-6}$ alkenyl, —$C_{2-6}$ alkynyl, —$C_{1-6}$ haloalkyl, —$OR^6$, —$SR^6$, —$NR^7R^8$, aryl and heteroaryl;
$R^{10}$ and $R^{11}$ are the same or different and are independently selected from hydrogen, —$C_{1-6}$ alkyl, —$C_{2-6}$ alkenyl, —$C_{2-6}$ alkynyl, —$C_{1-6}$ haloalkyl, aryl and heteroaryl;
m is 0 or 1;
wherein each alkyl, alkenyl, alkynyl, aryl and heteroaryl group may be optionally substituted;
or a pharmaceutically acceptable salt, hydrate or solvate thereof.

5. The method according to claim 4 wherein the method is for reversing the damage caused by cardiotoxic immunoglobulin light chains deposited in heart tissue.

6. The method according to claim 1 wherein R, $R^1$ and $R^3$ are all hydrogen.

7. The method according to claim 1 wherein $R^2$ is selected from heterocyclyl, —$CH_2$heterocyclyl, —$CO_2H$, —C(O)$NR^7R^8$, —$NR^7R^8$, —$CH_2NR^7R^8$, —CH=NOH, —CH=$NOC_{1-6}$ alkyl, —$CH_2OR^6$ or —$SO_2NR^{10}R^{11}$.

8. The method according to claim 7 wherein $R^2$ is selected from —C(O)NH(CH$_2$heterocyclyl), —C(O)NH(CH$_2$CH$_2$heterocyclyl), pyridyl, —$CH_2N(C_{1-3}$ alkyl$)_2$, —N($C_{1-3}$ alkyl)(heterocyclyl), —$CH_2NH(C_{1-3}$ alkyl), —CH=N—OH, —CH=N—$OCH_3$, —$CH_2OC_{1-6}$ alkyl, —$CH_2OC_{1-6}$ haloalkyl, —CH=$NCH_3$ and —$CH_2N(C_{1-3}$ alkyl)(CH$_2$heterocyclyl).

9. A method according to claim 1 wherein $R^4$ and $R^5$ are both Cl.

10. The method according to claim 1 wherein the compound of formula (I) is selected from:
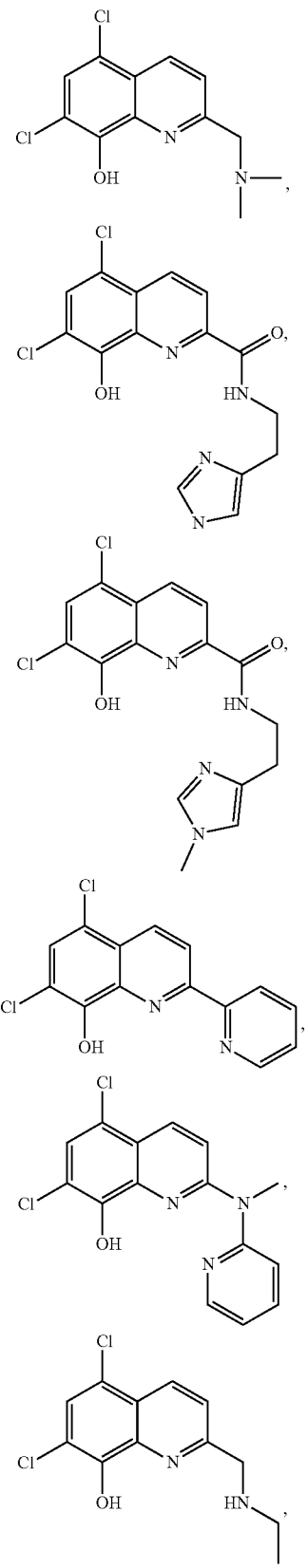
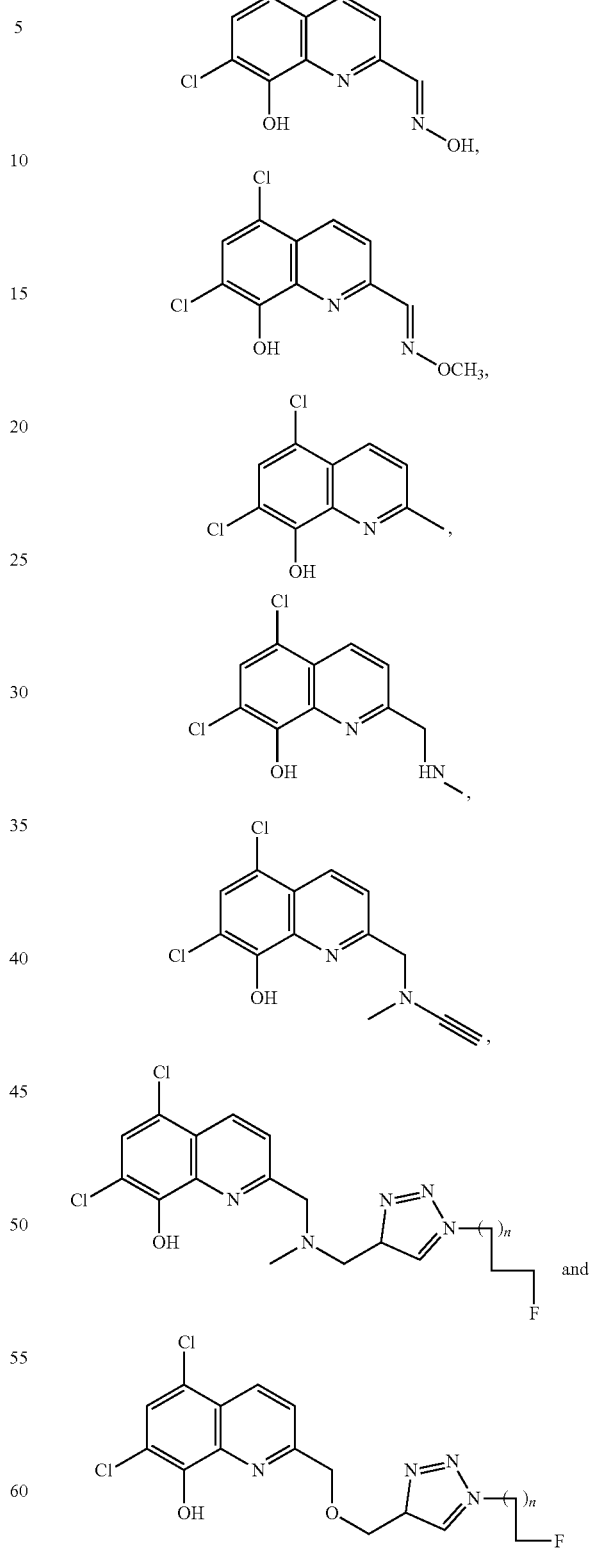
where n is 1, 2 or 3.
11. The method according to claim 1 further comprising administration of another pharmaceutically active agent.

12. The method according to claim 11 wherein the other pharmaceutically active agent is an antioxidant or a pharmaceutically active agent for treating immunoglobulin light chain amyloidosis.

13. A method of treating or alleviating or reversing the symptoms of immunoglobulin light chain amyloidosis comprising administering to a subject in need thereof an effective amount of a compound of formula (I)

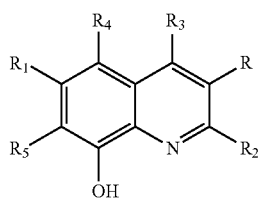

wherein
- R, $R^1$ and $R^3$ are the same or different and are each independently selected from hydrogen, —$C_{1-3}$ alkyl, —$C_{2-3}$ alkenyl, —$C_{2-3}$ alkynyl, —$CF_3$, —$CHF_2$, —$CH_2F$, —$CH_2CF_3$, —$CH_2CF_2H$, —$CH_2CH_2F$, —OH, —$OC_{1-6}$ alkyl, —$OCF_3$, —$OCHF_2$, —$OCH_2F$, —$OCH_2CF_3$, —$OCH_2CHF_2$, —$OCH_2CH_2F$, —$OC_{2-3}$ alkenyl, —$OC_{2-3}$ alkynyl, —$NH_2$, —$NH(C_{1-3}$ alkyl), —$N(C_{1-3}$ alkyl)$_2$, —$SO_2C_{1-6}$ alkyl, —$CO_2H$, —$CO_2C_{1-3}$ alkyl, —$CONH_2$, —$CONH(C_{1-3}$ alkyl), —$CON(C_{1-3}$ alkyl)$_2$, F, Cl and Br;
- $R^2$ is selected from —$(CH_2)_m$heterocyclyl, —$(CH_2)_mC(O)R^9$, —$(CH_2)_mCN$, —$(CH_2)_mNR^7R^8$, —CH=N$C_{1-6}$ alkyl, —CH=N—$OR^6$, —CH=N—$NR^{10}R^{11}$, —$SO_2NR^{10}R^{11}$ and —$(CH_2)_mOR^6$;
- $R^4$ and $R^5$ are the same or different and are independently selected from F, Cl and I;
- $R^6$ is selected from hydrogen, —$C_{1-6}$ alkyl, —$C_{2-6}$ alkenyl, —$C_{2-6}$ alkynyl, —$C_{1-6}$ haloalkyl, aryl and heteroaryl;
- $R^7$ and $R^8$ are the same or different and are independently selected from hydrogen, —$C_{1-6}$ alkyl, —$C_{2-6}$ alkenyl, —$C_{2-6}$ alkynyl, —$C_{1-6}$ haloalkyl, —$(CH_2)_m$aryl and —$(CH_2)_m$heterocyclyl, or $R^7$ and $R^8$ taken together form a heterocyclic ring;
- $R^9$ is selected from hydrogen, —$C_{1-6}$ alkyl, —$C_{2-6}$ alkenyl, —$C_{2-6}$ alkynyl, —$C_{1-6}$ haloalkyl, —$OR^6$, —$SR^6$, —$NR^7R^8$, aryl and heteroaryl;
- $R^{10}$ and $R^{11}$ are the same or different and are independently selected from hydrogen, —$C_{1-6}$ alkyl, —$C_{2-6}$ alkenyl, —$C_{2-6}$ alkynyl, —$C_{1-6}$ haloalkyl, aryl and heteroaryl;
- m is 0 or 1;
- wherein each alkyl, alkenyl, alkynyl, aryl and heteroaryl group may be optionally substituted; or a pharmaceutically acceptable salt, hydrate or solvate thereof; and an effective amount of an antioxidant.

14. The method according to claim 13 wherein the symptoms treated, alleviated or reversed are associated with cardiotoxic immunoglobulin light chain deposits in heart tissue.

15. The method according to claim 13 wherein the effective amount of the compound of formula (I) is a sub-therapeutic amount.

16. The method according to claim 13 wherein the compound of formula (I) is

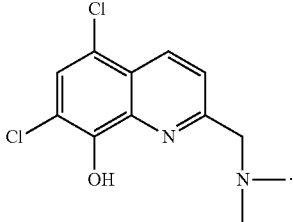 [SMILES: CN(C)Cc1ccc2c(Cl)cc(Cl)c(O)c2n1]

17. The method according to claim 13 wherein the antioxidant is tetracycline.

* * * * *